(12) United States Patent
Chen et al.

(10) Patent No.: US 12,220,550 B2
(45) Date of Patent: Feb. 11, 2025

(54) TRANSDERMAL DELIVERY DEVICE, METHODS OF USING AND MAKING THE SAME

(71) Applicant: BUDDHIST TZU CHI MEDICAL FOUNDATION, Haulien (TW)

(72) Inventors: Yu-Shuan Chen, Haulien (TW);
Hsieh-Chih Tsai, Haulien (TW);
Chang-Yi Lee, Haulien (TW); Haile Fentahun Darge, Haulien (TW);
Shinn-Zong Lin, Haulien (TW);
Tzyy-Wen Chiou, Haulien (TW);
Chia-Yu Chang, Haulien (TW)

(73) Assignee: BUDDHIST TZU CHI MEDICAL FOUNDATION, Haulien (TW)

( * ) Notice: Subject to any disclaimer, the term of this patent is extended or adjusted under 35 U.S.C. 154(b) by 511 days.

(21) Appl. No.: 17/454,750

(22) Filed: Nov. 12, 2021

(65) Prior Publication Data
US 2023/0149678 A1    May 18, 2023

(51) Int. Cl.
| | |
|---|---|
| *A61M 37/00* | (2006.01) |
| *C08F 220/38* | (2006.01) |
| *C08F 220/56* | (2006.01) |

(52) U.S. Cl.
CPC ..... *A61M 37/0015* (2013.01); *C08F 220/387* (2020.02); *C08F 220/56* (2013.01); *A61M 2037/0023* (2013.01); *A61M 2037/0046* (2013.01); *A61M 2037/0053* (2013.01); *A61M 2205/02* (2013.01); *A61M 2207/10* (2013.01)

(58) Field of Classification Search
CPC ...... A61M 37/0015; A61M 2037/0023; A61M 2037/0046; A61M 2037/0053; A61M 2205/02; A61M 2207/10; A61M 2037/0061; C08F 220/387; C08F 220/56
See application file for complete search history.

(56) References Cited

U.S. PATENT DOCUMENTS

| | | | | |
|---|---|---|---|---|
| 2008/0269685 | A1* | 10/2008 | Singh | A61K 9/0021 604/173 |
| 2017/0020941 | A1* | 1/2017 | Naheed | A61M 37/0015 |
| 2021/0393543 | A1* | 12/2021 | Wu | A61K 9/7023 |

OTHER PUBLICATIONS

Li, Wei et al. "Rapidly separable microneedle patch for the sustained release of a contraceptive" Nature Biomedical Engineering, https://doi.org/10.1038/s41551-018-0337-4, Jan. 14, 2019 (12 pages).
Liu, Tianqi et al. "Fabrication of Rapidly Separable Microneedles for Transdermal Delivery of Metformin on Diabetic Rats" Journal of Pharmaceutical Sciences 110 (2021) 3004?3010 (7 pages).
Fentahun Darge, Haile et al. "Multifunctional drug-loaded micelles encapsulated in thermo-sensitive hydrogel for in vivo local cancer treatment: Synergistic effects of anti-vascular and immuno-chemotherapy" Chemical Engineering Journal 406 (2021) 126879 (20 pages).

* cited by examiner

*Primary Examiner* — Nathan R Price
*Assistant Examiner* — Adam J. Cermak
(74) *Attorney, Agent, or Firm* — Osha Bergman Watanabe & Burton LLP

(57) ABSTRACT

Provided is a device for transdermal delivery of drugs. The device includes a separable substrate and is loaded with dual drugs based on an interpenetrating polymer network hydrogel. Also provided are methods of making and using the transdermal delivery device.

19 Claims, 36 Drawing Sheets
(2 of 36 Drawing Sheet(s) Filed in Color)

TRANSDERMAL DELIVERY DEVICE, METHODS OF USING AND MAKING THE SAME

BACKGROUND

1. Technical Field

The present disclosure pertains to a transdermal drug delivery device having a substrate and a plurality of projections made from interpenetrating polymer network hydrogel for loading and delivering drugs.

2. Description of Related Art

The technology field of drug delivery works on delivering medications to target sites at different organs and aims to enhance drug efficacy and minimize side effects by controlling drug release.

So far, there are many ways of drug delivery into human body for cancer treatment, which are generally divided into oral, parenteral route of injection (intravenous, intramuscular or subcutaneous) and transdermal drug delivery.

However, either oral administration or parenteral route of injection have several limitations that compromise their effectiveness; for example, oral drug administration results in enzymatic digestion and possible side effects on liver, as it passes through liver before joining the blood circulation for therapeutic effects. In addition, off-targeting delivery is associated with adverse side effects, in which the injection can be detrimental and painful for patients and particularly increase the risk of infection. Therefore, an effective delivery route for cancer treatment is highly sought after.

To overcome the said limitations via oral route drug administration or parenteral route injection, microneedles (MN) have been developed to create micro size pathways on the skin which allow molecular drugs to enter and reach the target site as a device for transdermal drug administration. The transdermal administration is a patient-friendly and safe way of delivering drugs by applying drug formulations to skin surface where the drugs are intended to diffuse into the body circulation system. For instance, the transdermal drug administration offers many advantages over oral administration or parenteral injection and includes effective delivery and attractable for local immune activation and subsequent therapeutic upshot in cancer treatment. MNs-mediated transdermal drug delivery is also advantageous over the conventional intravenous, intramuscular or subcutaneous drug delivery administration in minimizing the risk of drug metabolism before its effect, and also reduces the frequency of administration.

However, unlike silicon or metal derived MNs, the biodegradable polymeric MNs manufactured using those conventional methods present problems such as bending and deformation during administration into the skin due to lack of sufficient mechanical strength. In this regard, the polymerization method and the types of monomers are issues to be considered for regulating mechanical strength and rate of degradation of MNs to penetrate the skin and enhance drug release, respectively.

Therefore, there is an unmet need for an improved microneedle device which is adequate in mechanical properties and easy to use on skin surfaces.

SUMMARY

The present disclosure provides a solution to many drawbacks of earlier microneedles by providing a transdermal delivery device which comprises a plurality of projections each including a first polymer formed of a first monomer with a first linkage and a second polymer formed of a second monomer with a second linkage; a substrate including a third polymer formed of the first monomer with a third linkage; and a bioactive agent comprised in one of the plurality of projections, wherein the plurality of projections are coupled to the substrate and configured to be at least partially insertable into skin of a subject in need thereof, and the substrate is configured to be removed with a compound targeted to break the third linkage forming the third polymer in the substrate after the transdermal delivery device is applied to the skin for a predetermined time.

Due to improved mechanical and chemical properties, the plurality of projections of the present disclosure forming microneedles (MNs) are useful in applications for which existing MNs have failed. Performance in existing applications is improved with MNs described herein. For example, the improved MNs described herein are useful in applications where existing MNs lack sufficient mechanical strength for, e.g., penetration into the stratum corneum and other biological tissues such as blood vessels, heart valves, muscles, and skin, piercing the outer layers of skin, and permeability of the compounds into the blood stream. The improved MNs described herein are also useful in transdermal drug delivery and tumor growth suppression. The disclosure also provides methods of making MNs and treating cancer by decreasing a tumor mass and increasing immune activation response around tumor sites.

The present disclosure provides a device comprising an interpenetrating polymer network (IPN) hydrogel. In at least one embodiment, the hydrogel comprises sodium alginate and sulfobetaine methacrylate (SBMA), which are sequentially photo-crosslinked with N,N'-methylenebisacrylamide (MBAAm) followed by ionic crosslinking with calcium ions. The device further comprises a separable substrate comprising an IPN hydrogel crosslinked with a disulfide linker, N,N-bisacryloylcystine (BISS), wherein the disulfide bonds are cleaved by dithiothreitol (DTT) and/or ethylenediaminetetraacetic acid (EDTA) and separable from the MNs array.

The present disclosure provides a drug delivery device loaded with dual drugs, for example, lipopolysaccharide (LPS) and doxorubicin (DOX), for synergistic immuno-chemotherapeutic outcome. LPS is a well-explored immune-stimulatory macromolecule composed of lipids and polysaccharides and able to reprogram tumor-associated macrophages (TAMs) to M1-like phenotype which have antitumor functions by secreting potent antitumor inflammatory cytokines such as tumor necrosis factor-$\alpha$ (TNF-$\alpha$). It has been reported that the inflammatory cytokines provide a synergistic therapeutic effect with various anti-cancer drugs, such as doxorubicin (DOX), dactinomycin and etoposide. LPS further induces activation of antigen presenting cells and T-cells including CD4+, CD8+ and CD25+ and others for cancer immunosurveillance. Adequate amounts of drugs are released from the MNs in the first 24 hours (h), followed by a very gradual and sustained release for the next 7 days. For example, 66.1±7.4% and 59.4±5.5% of DOX and LPS are released in the first 24 hours, respectively. In at least one embodiment, an in vivo study proves that the presence of LPS augments the expression and activation of immune-regulators and enhances the immuno-chemotherapeutic value synergistically. As a result, dual drugs-loaded MNs such as LPS and DOX-loaded MNs induce significant tumor inhibition on glioma-bearing C57BL/6 mice than individual drugs ($p<0.05$). Therefore, MNs-mediated transdermal delivery of combined drugs to the proximity of subcutaneous tumor is an effective approach for efficiently administering drugs and enhances therapeutic efficacy with negligible systemic adverse effects.

In at least one embodiment, the present disclosure provides a drug delivery device comprising a separable and mechanically strong MNs patch which withstands up to 0.64 N/needle for efficient transdermal drug delivery. In at least one embodiment, the MNs further comprise a disulfide bond crosslinking agent to form a separable substrate, which is disintegrated and removed with a reducing agent or a metal chelator such as a DTT and/or EDTA solution while the MNs arrays remain inside the skin for sustained transdermal release of drugs.

In at least one embodiment, the present disclosure provides a drug delivery device in the form of MNs arrays loaded with, e.g., dual drugs, to be applied transdermally, and then a separable substrate of the MNs is removed with a dithiothreitol (DTT) and/or ethylenediaminetetraacetic acid (EDTA) solution. In at least one embodiment, the MNs arrays comprise an interpenetrating polymer network hydrogel with a separable substrate, wherein the interpenetrating polymer network hydrogel comprises sodium alginate and SBMA monomers, wherein the sodium alginate and SBMA are photo-crosslinked with MBAAm and ionically crosslinked with calcium ions. In some embodiments, the separable substrate comprises a disulfide linker, for example, N,N-bisacryloylcystine.

The present disclosure provides a transdermal delivery device, comprising a plurality of projections each including a first polymer formed of a first monomer with a first linkage and a second polymer formed of a second monomer with a second linkage; a substrate including a third polymer formed of the first monomer with a third linkage; and a bioactive agent comprised in one of the plurality of projections, wherein the plurality of projections are coupled to the substrate and configured to be at least partially insertable into skin of a subject in need thereof, and the substrate is configured to be removed with a compound targeted to break the third linkage forming the third polymer in the substrate after the transdermal delivery device is applied to the skin for a predetermined time.

In at least one embodiment, the first monomer is a zwitterion. In some embodiments, the zwitterion is phosphorylcholine, sulfobetaine, pyridinium alkyl sulfonate, carboxybetaine, phosphobetaine, phosphonobetaine, phosphinobetaine, ammoniosulfate, ammoniosulfonamide, pyridiniocarboxylate, or sulfoniocarboxylate. In at least one embodiment, the phosphorylcholine is phosphorylcholine acrylate, phosphorylcholine acrylamide, phosphorylcholine methacrylate, alkoxydicyanoethenolate or 2-methacryloyloxyethyl phosphorylcholine. In at least one embodiment, the sulfobetaine is sulfobetaine acrylate, sulfobetaine acrylamide, sulfobetaine methacrylate, sulfobetaine vinylimidazole or sulfobetaine vinylpyridine. In at least one embodiment, the carboxybetaine is carboxybetaine acrylate, carboxybetaine methacrylate, carboxybetaine acrylamide, carboxybetaine vinylimidazole, carboxybetaine methacrylamide, carboxybetaine isobutylene, or carboxybetaine diallylamine. In at least one embodiment, the pyridinium alkyl sulfonate is 3-(2-vinylpyridinium-1-yl)propane-1-sulfonate, N-(2-methacryloyloxy) ethyl-N,N-dimethylammoniopropanesulfonate or N-(3-methacryloylimino) propyl-N,N-dimethylammoniopropanesulfonate.

In at least one embodiment, the second polymer is one or more selected from the group consisting of a biocompatible synthetic polymer, a semisynthetic polymer and a natural polymer. In at least one embodiment, the second polymer is selected from the group consisting of gum, polysaccharide, a polysaccharide derivative, alginate including sodium alginate or calcium alginate, chitosan, a chitosan derivative, collagen, gelatin, dextran, poly(vinylpyrrolidone), hydroxyethyl (heta) starch, polyethylene glycol, functionalized dextran, glycopolymer containing trehalose, hyaluronic acid, methacrylated hyaluronic acid, poly(methyl vinyl ether), poly(methyl vinyl ether-alt-maleic anhydride), poly(lactic acid), polyglycolide, poly(lactic-co-glycolic acid), polycarbonate, poly (vinyl alcohol), poly(hydroxyethyl methacrylate), poly(vinylpyrrolidone), (2-carboxymethyl)-3-acrylamidopropyl dimethylammonium bromide, (2-carboxymethyl)-3-acrylamidopropyl dimethylammonium bromide-co-hydroxyethyl methacrylate, (2-carboxymethyl)-3-acrylamidopropyl dimethylammonium bromide-co-acrylamide, methacrylated (2-carboxymethyl)-3-acrylamidopropyl dimethylammonium bromide-co-acrylamide, poly (ε-caprolactone) poly (ε-caprolactone-co-glycolic acid), poly (2-methacryloyloxyethyl phosphorylcholine), poly (carboxybetaine) vinylimidazole, poly (sulfobetaine) vinylimidazole, and poly (sulfobetaine) vinylpyridine.

In at least one embodiment, the first monomer is crosslinked by a chemical linkage and the second monomer is crosslinked by a physical linkage. In at least one embodiment, the chemical linkage and the physical linkage form an interpenetrating polymer network. In at least one embodiment, the chemical linkage is formed by at least one crosslinking agent selected from the group consisting of N,N'-methylene-bisacrylamide (MBA), diacryloyl derivative of cystine (BISS), dimethylsubermidate, glutaraldehyde, N,N-ethylene-bis (iodoacetamide), ethylene glycol dimethacrylate (EGDM), poly (ε-caprolactone) diacrylate, polylactide diacrylate, polylactide dimethacrylate, poly (lactide-co-glycolide) diacrylate, poly (lactide-co-glycolide) dimethacrylate, poly (ε-caprolactone-b-ethylene glycol-b-ε-caprolactone) diacrylate, glycol-b-(lactide-co-glycolide) dimethacrylate, a polymerizable compound including a disulfide bond, a peptide bond or an ester bond, poly (-caprolactone) dimethacrylate (MAC-PCL-MAC), poly (ε-caprolactone-b-ethylene glycol-b-ε-caprolactone) dimethacrylate (MAC-PCL-PEG-PCL-MAC), poly (lactide-b-ethylene glycol-b-lactide) diacrylate (AC-PLA-PEG-PLA-AC), poly (lactide-b-ethylene glycol-b-lactide) dimethacrylate (MAC-PLA-PEG-PLA-MAC), poly [(lactide-co-glycolide)-b-ethylene glycol-b-(lactide-co-glycolide)] diacrylate (AC-PLGA-PEG-PLGA-AC), poly [(lactide-co-glycolide)-b-ethylene glycol-b-(lactide-co-glycolide)] dimethacrylate (MAC-PLGA-PEG-PLGA-MAC), poly (ε-caprolactone-co-lactide)-diacrylate (AC-PCLA-AC), poly (ε-caprolactone-co-lactide)- dimethacrylate (MAC-PCLA-MAC), poly (ε-caprolactone-co-glycolide) diacrylate (AC-PCGA-AC), poly (ε-caprolactone-co-glycolide) dimethacrylate (MAC-PCGA-MAC), poly (εcaprolactone-co-lactide)-b-ethyleneglycol-b-(εcaprolactone-co-lactide) diacrylate (AC-PCLA-PEG-PCLA-AC), poly (ε-caprolactone-co-lactide)-b-ethyleneglycol-b-(ε-caprolactone-co-lactide) dimethacrylate (MAC-PCLA-PEG-PCLA-MAC), poly (ε-caprolactone-co-glycolide)-b-ethyleneglycol-b-(ε-caprolactone-co-glycolide) diacrylate (AC-PCGA-PEG-PCGA-AC), poly (ε-caprolactone-co-glycolide)-b-ethyleneglycol-b-(ε-caprolactone-co-glycolide) dimethacrylate (MAC-PCGA-PEG-PCGA-MAC).

In at least one embodiment, a ratio between the first monomer and the second monomer is about 1:1, about 1:2, about 1:3, about 1:4, about 1:5, about 2:1, about 3:1, about 4:1 or about 5:1.

In at least one embodiment, the third linkage is a disulfide bond. In at least one embodiment, the compound targeted to break the third linkage forming the third polymer in the substrate is dithiothreitol (DTT), ethylenediaminetetraacetic acid (EDTA), glutathione (GSH), β-mercaptoethanol or L-cysteine.

In at least one embodiment, the plurality of projections each have a shape tapered to a point. In at least one embodiment, the plurality of projections each have a pyramidal shape or a conical shape. In at least one embodiment, the plurality of projections each have a height of between about 25 μm to about 2,500 μm, a width of between about 50 μm to about 250 μm, and a diameter of tip between about 1 μm to about 25 μm.

The present disclosure further provides a method of fabricating a transdermal delivery device, comprising: preparing a first solution including a first monomer, a second monomer, a first crosslinking agent and at least one bioactive agent; preparing a second solution including the first monomer and a second crosslinking agent; applying the first solution including the at least one bioactive agent to an inverse mold and subjecting the first solution to centrifuge; after centrifugation, removing an upper layer of the first solution and applying the second solution on a top of the inverse mold; covering the inverse mold with a cover mold and subjecting to centrifuge; applying a first condition suitable to cause solidification of the first solution to form a plurality of projections; applying a second condition suitable to cause solidification of the second condition to form a substrate; and demolding the plurality of projections and the substrate from the inverse mold to obtain the transdermal delivery device.

The present disclosure further provides a method of inducing a biological activity in a subject in need thereof, comprising: providing the transdermal delivery device described above; applying the transdermal delivery device to the skin of the subject for the plurality of projections to puncture the skin of the subject; and removing the substrate of the transdermal delivery device from the subject with a compound targeted to break the third linkage forming the third polymer in the substrate, with the plurality of projections including the bioactive agent to be remained in the skin.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 6A is a line graph of tensile test of IPN hydrogel at different cross-linking conditions; FIG. 6B is a line graph of tensile test of IPN hydrogel at different monomer ratios; and FIG. 6C is a line graph of compressive stress of MNs patch fabricated with 1:1-Uv 60, $Ca^{2+}$ 30.

DETAILED DESCRIPTION OF THE EMBODIMENTS

Figure 1A:
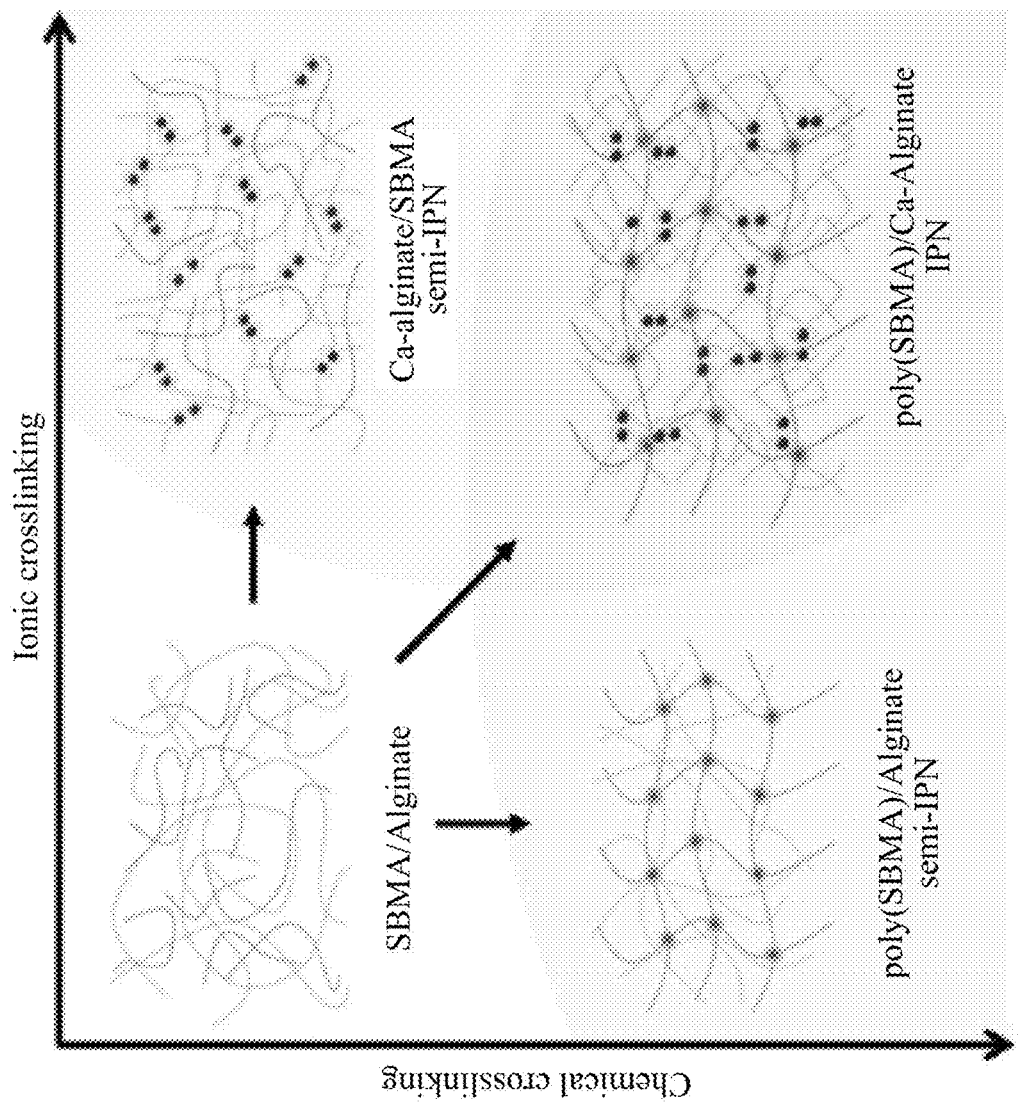
FIG. 1A is a schematic illustration of IPN hydrogel that shows the interpenetrating polymer network (IPN) hydrogel adopting sequential chemical crosslinking of SBMA network followed by ionic crosslinking of alginate network with calcium ions ($Ca^{2+}$) for fabricating relatively tough MNs arrays.

Referencing to figures which constitute a portion of the detailed description of examples, the embodiments for implementation of the disclosure are illustrated. It should be understood that other examples can be used, and alternations also can be made without departing from the scope of the disclosure.

Unless otherwise stated herein, the singular form "a," "an" and "the" used in this description and the attached claims should be considered to encompass the singular and the plural forms, unless it is otherwise stated or obviously contradictory to the context.

The term "about" used herein refers to be approximate or close to in the context of a value. In an example, the term "about" may comprise traditional rounding based on the significant number of the value. In addition, the phrase "about x to y" comprises "about x to about y."

Unless otherwise stated herein, the term "or" used in this description and the attached claims typically comprises the use in the meaning of "and/or." As used herein and unless otherwise stated, the conjunction "and" is intended to be inclusive, and the conjunction "or" is not intended to be exclusive. For example, the phrase "or alternatively" is intended to be exclusive.

Unless otherwise stated herein, the terms "comprise," "have," "include" and "contain" should be considered to be open terms (i.e., means "includes but not limited to").

Unless otherwise stated herein, the statement of a value range is only for the purpose of abbreviation of all single values falling into the range, and each single value is incorporated in the specification as if it is stated individually herein.

Unless otherwise stated herein or contradictory to the context, all methods described herein can be performed in any appropriate order. Unless otherwise required, the use of any and all examples or exemplary words (e.g., "such as" and "for example") is only for setting forth of the disclosure rather than forming restriction to the scope of the disclosure.

As used herein, the term "preventing" or "prevention" is defined as a probability for elimination or reduction of the occurrence of one or more symptom(s) of a cancer or tumor.

For example, the composition described herein can be used for treating tumors or reducing tumor cells or treating cancer or reducing cancer cells.

As used herein, the term "treating" or "treatment" is directed to the administration of an effective dose of anti-cancer drug to a subject in need thereof to cure, relieve, treat, improve or prevent the cancer, the symptoms thereof or the risk to develop the cancer. The subject can be identified by a medical care professional based on the results from any appropriate diagnostic method.

As used herein, the term "adequate dose of drugs" refers to a treatment dosage which is sufficient to result in preventing the development, recurrence or onset of cancers and one or more symptoms thereof, enhancing or improving the prevention effect of another therapy, reducing severity and phases of cancer, improving one or more symptoms of cancer, preventing progression of cancer, and/or enhancing or improving the therapeutic effect of another therapy.

As used herein, the term "subject" is any organism in need of treatment and/or prevention for cancer. In at least one example, the subject is a mammal including but not limited to human, a domesticated animal (e.g., a rat and a mouse).

Figure 6C:
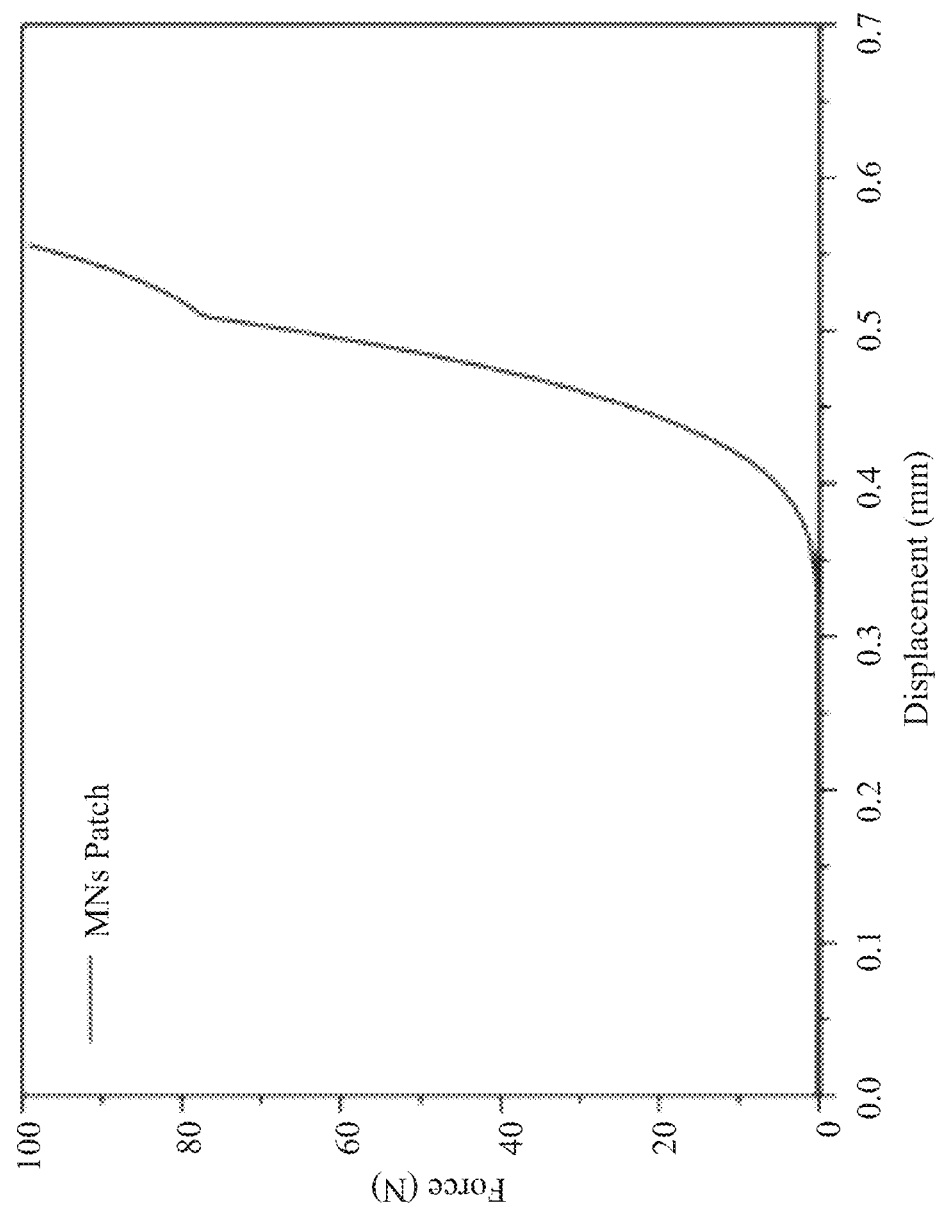
Figure 7:
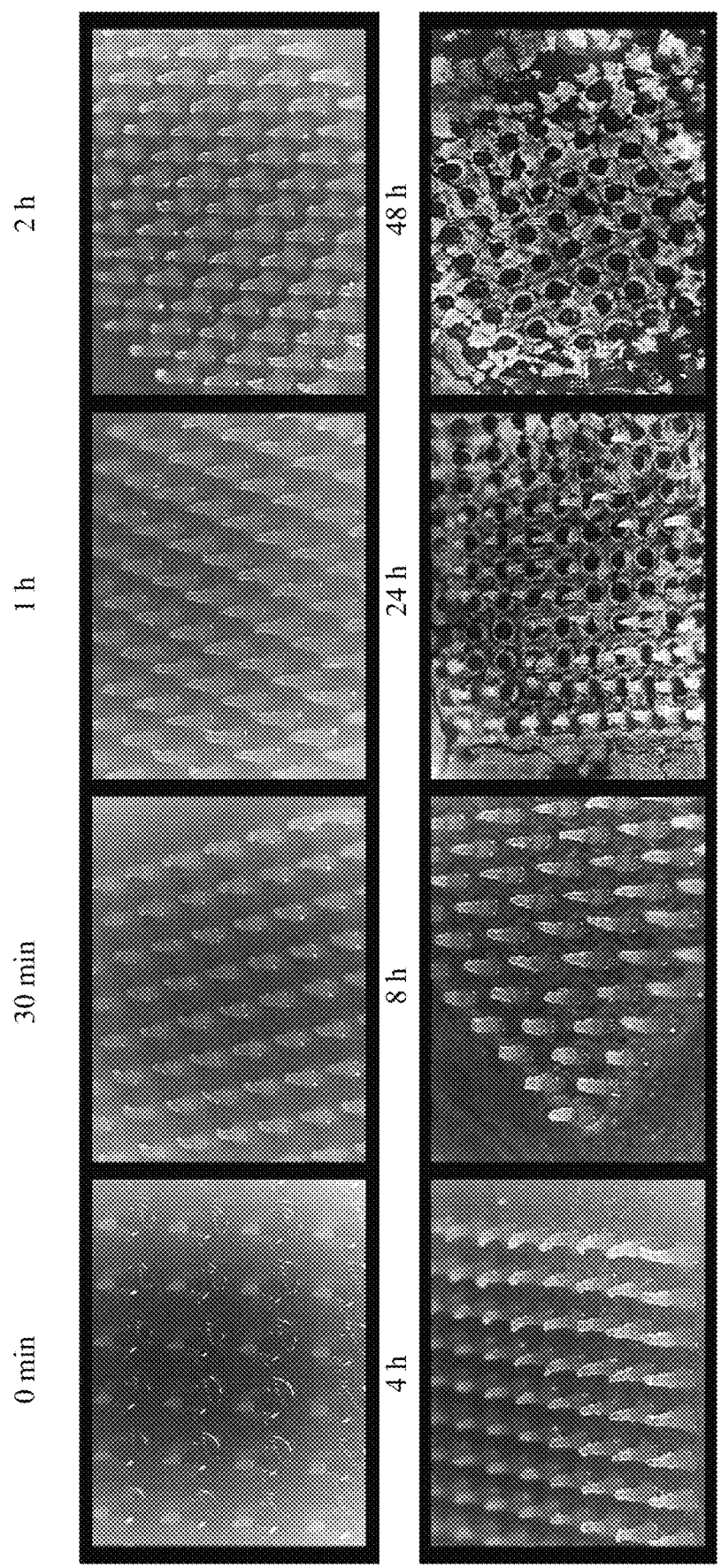
FIG. 7 is a series of microscopic images of the morphological changes of MNs immersed in PBS solution (pH 7.4) at 37° C. as a function of time.
Figure 10A:
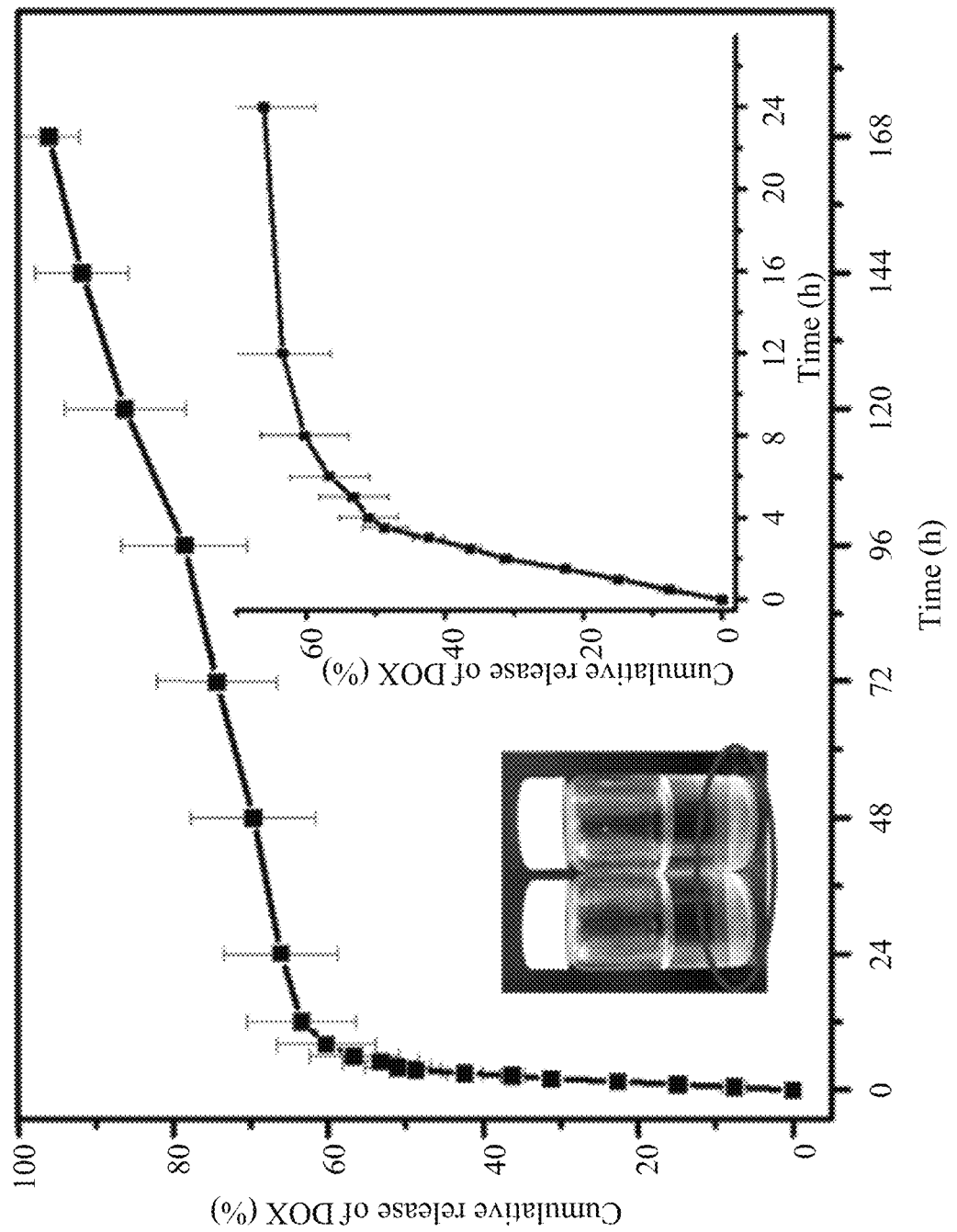
FIG. 10A is a line curve graph showing in vitro drug release of IPN hydrogel MNs (n=3), which is a cumulative release of DOX.
Figure 10B:
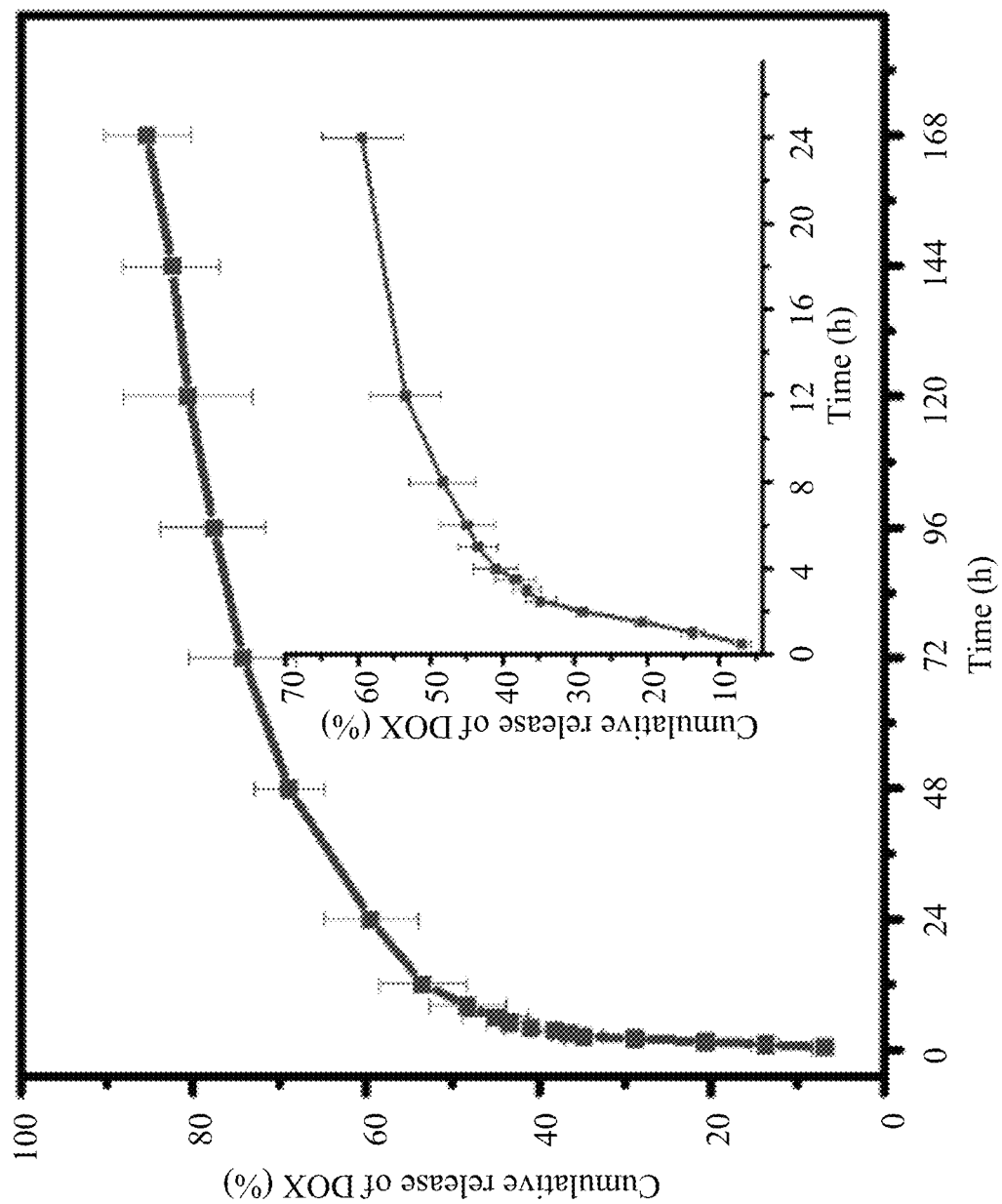
FIG. 10B is a line graph showing in vitro drug release of IPN hydrogel MNs (n=3), which is a cumulative release of LPS.
Figure 11A:
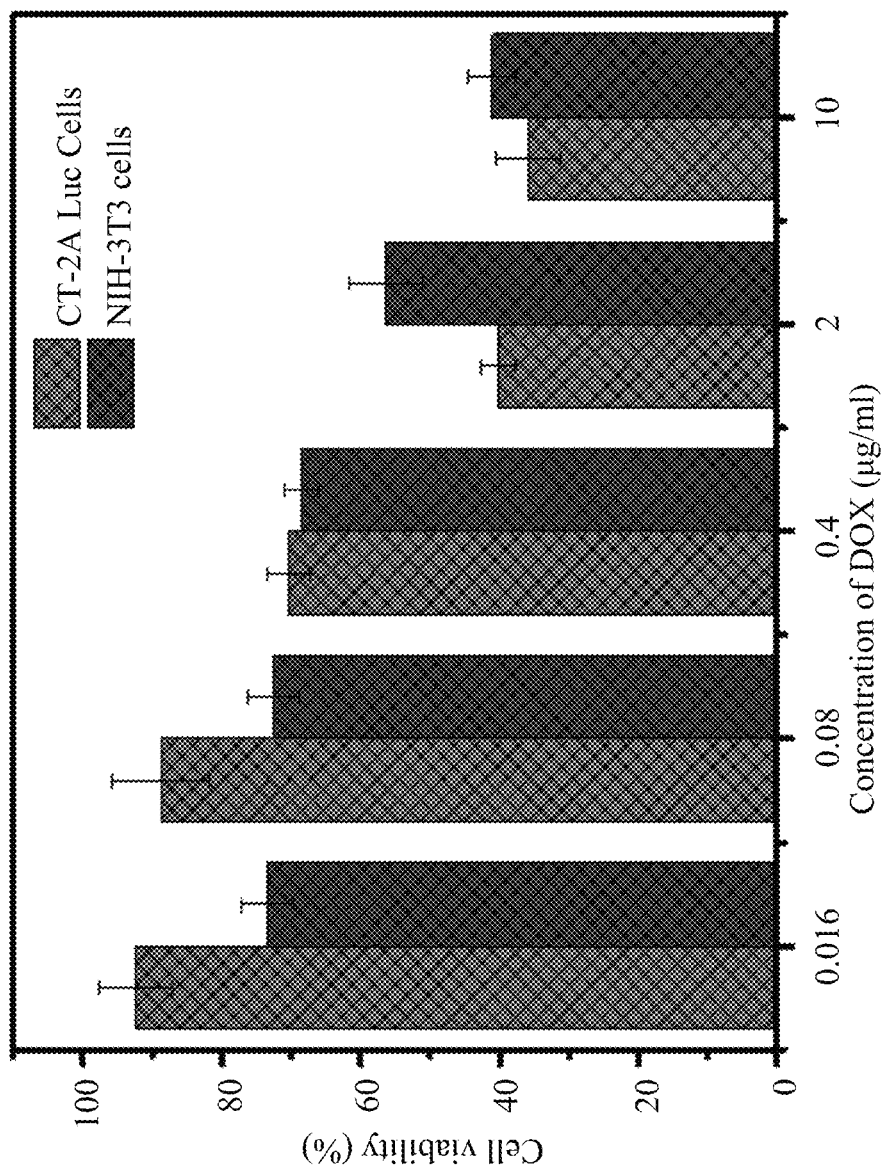
FIG. 11A is a bar graph showing chemo-toxic effect of DOX released from MNs on CT-2A-Luc cells and NIH-3T3 cells.
Figure 11B:
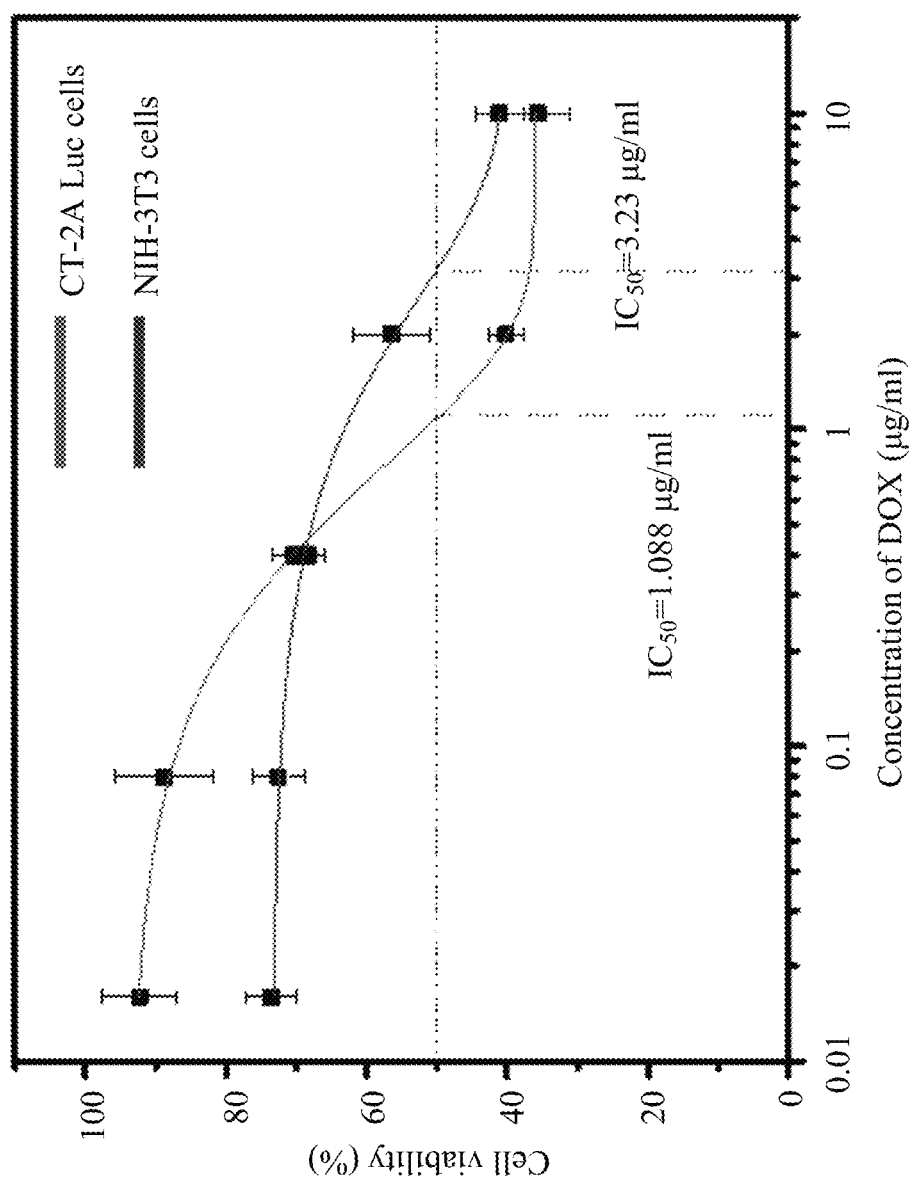
FIG. 11B is a line graph showing $IC_{50}$ trend line of DOX released from MNs in CT-2A-Luc cells and NIH-3T3 cells (n=8).
Figure 12A:
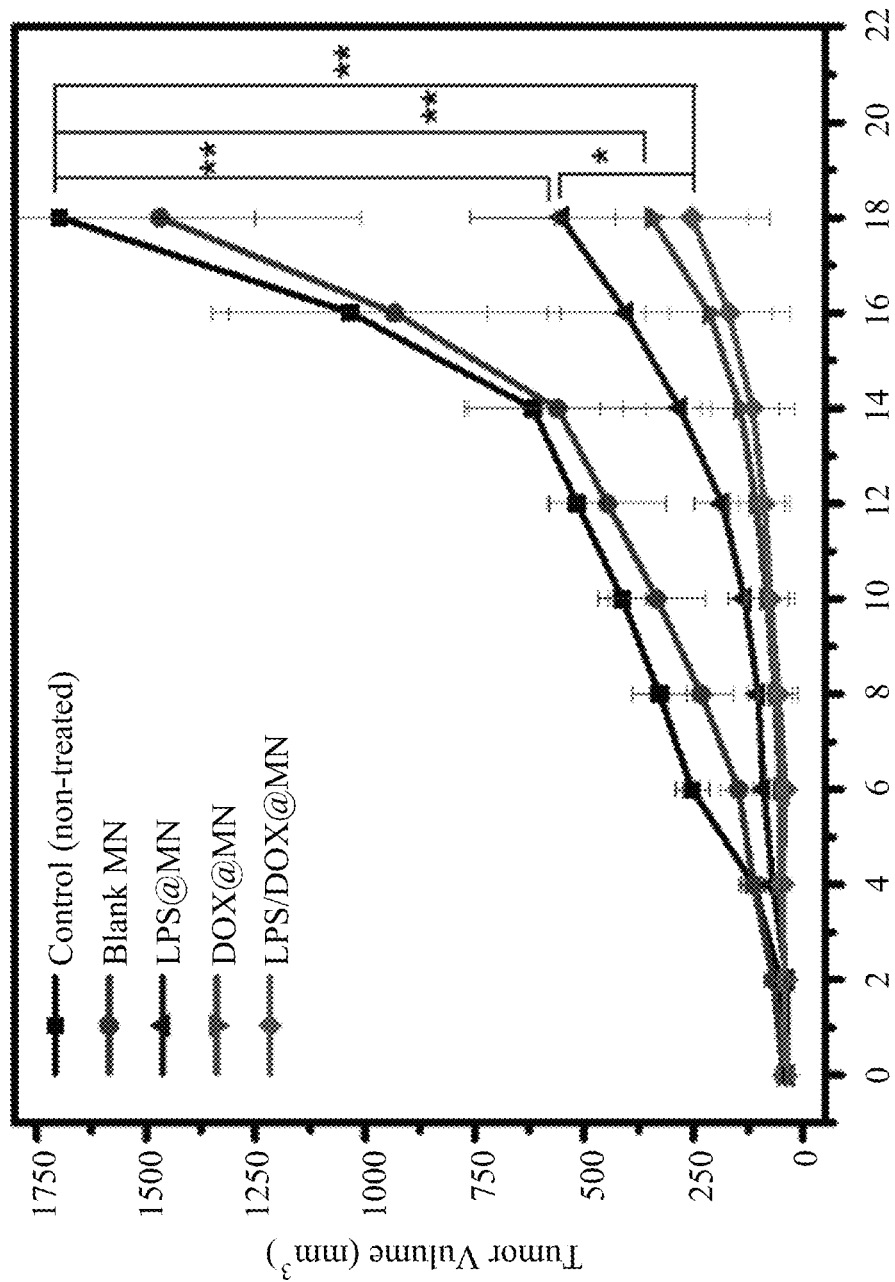
FIG. 12A is a line graph showing in vivo tumor suppression of drug loaded MNs, specifically tumor volume during treatment period.
Figure 12B:
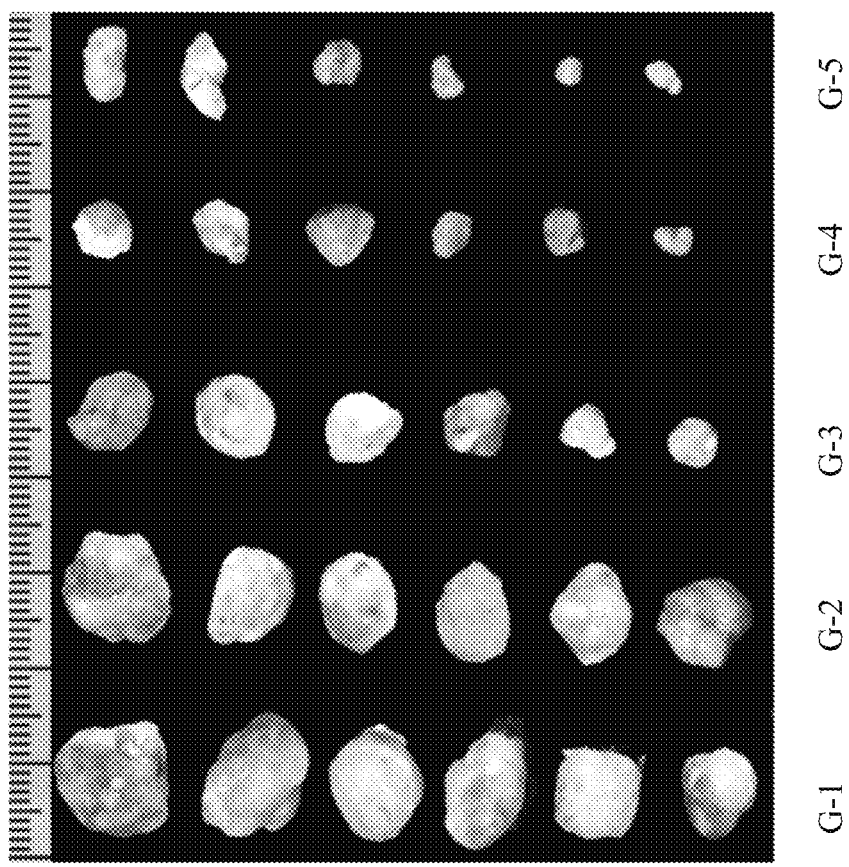
FIG. 12B is a photograph showing parallel trends that the size of tumors treated with LPS/DOX loaded MNs is significantly smaller than other formulations.
Figure 12C:
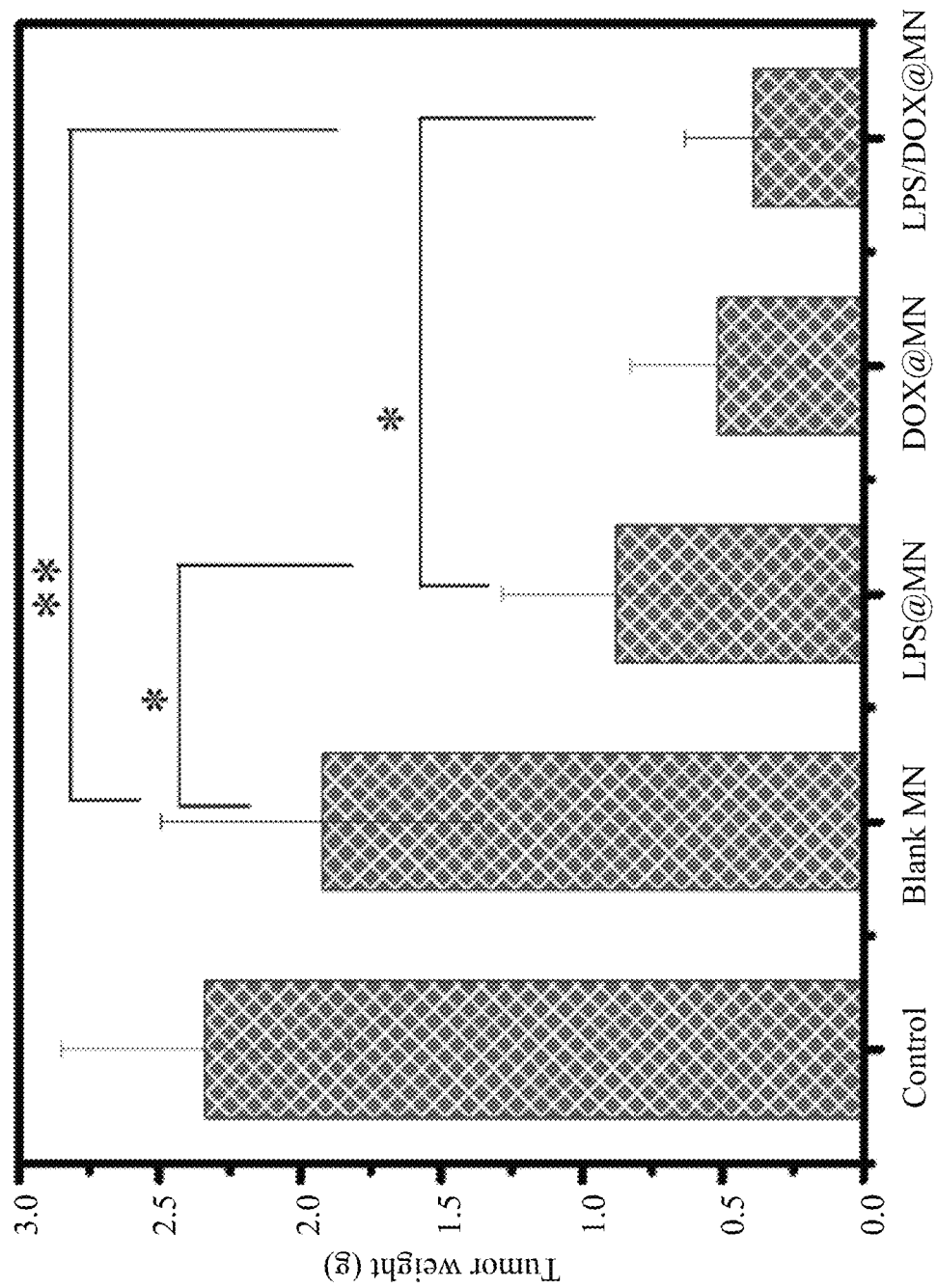
FIG. 12C is a bar graph showing the weight of tumor after dual drugs (LPS/DOX loaded MNs) or individual drugs (LPS loaded MNs or DOX loaded MNs) treatment for 18 days.
Figure 12D:
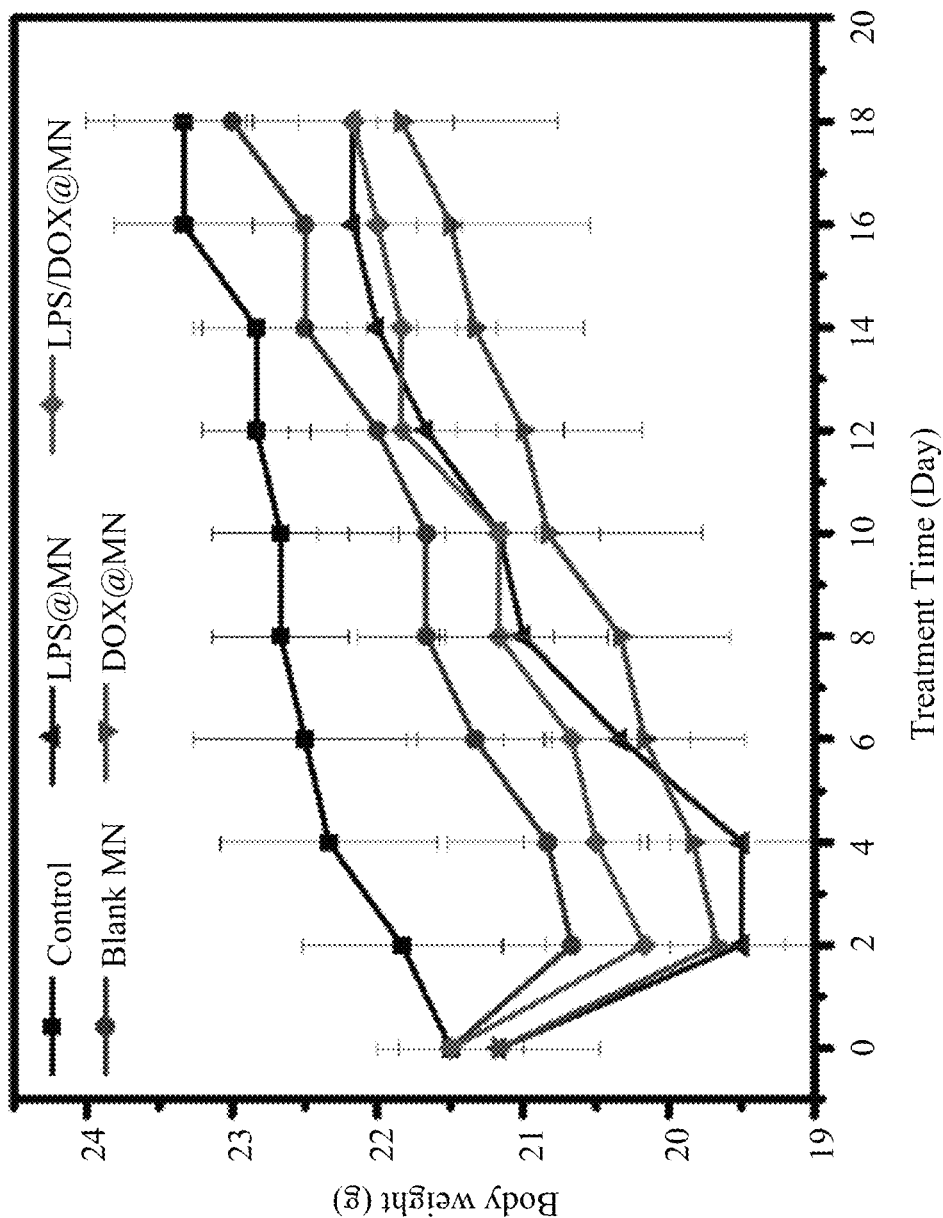
FIG. 12D is a line graph showing the body weight of mice treated with MNs vs. body weight of control group.
Figure 13A:
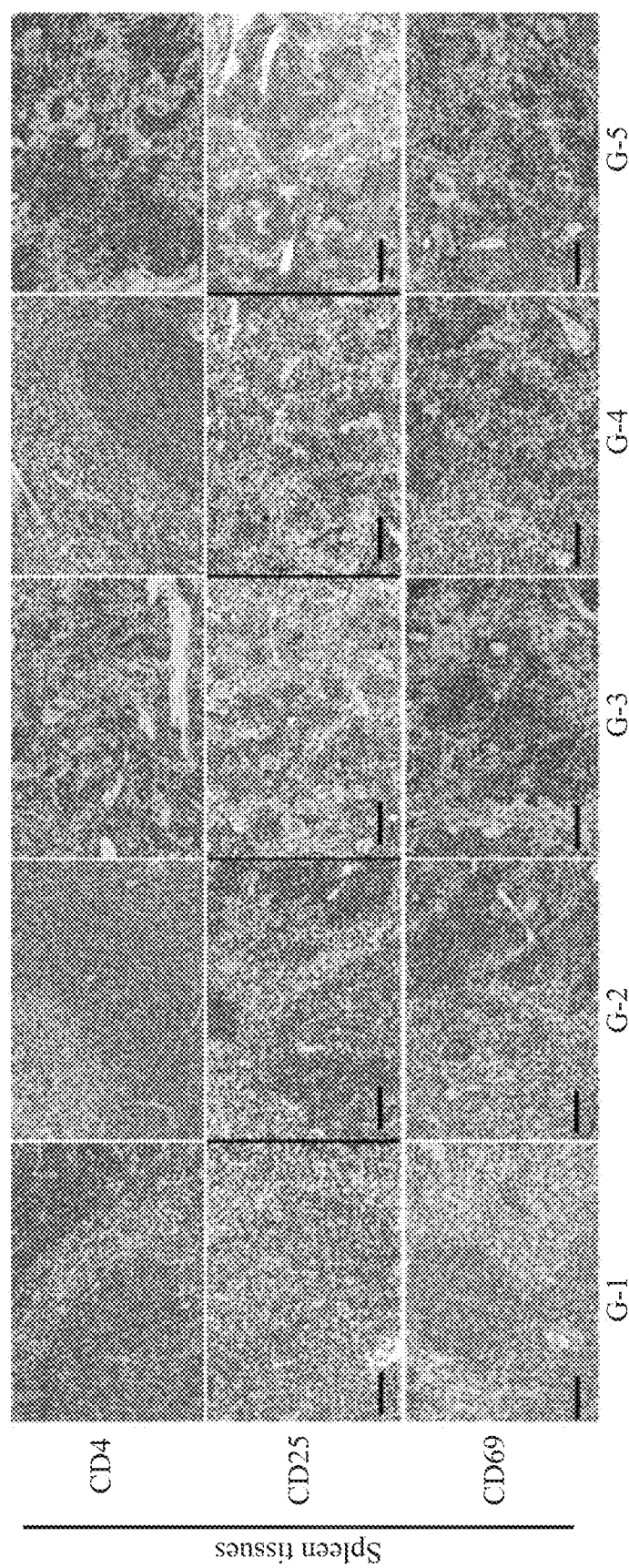
FIGS. 13A and 13B are immunohistochemistry (IHC) stains of the spleen and tumor tissues.
Figure 13B:
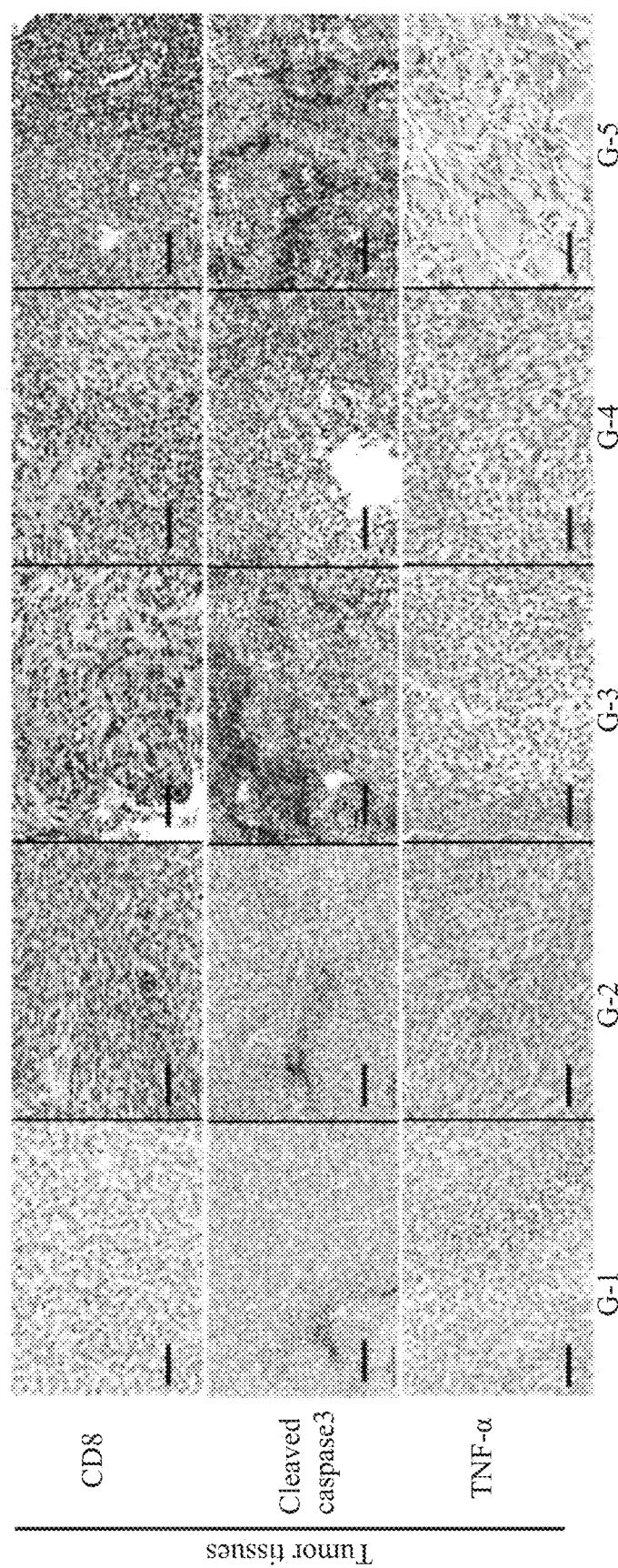

The interpenetrating polymer network hydrogel-based drug delivery device having a separable substrate for transdermal drug delivery described herein overcomes limitations of earlier network hydrogels. The improved interpenetrating polymer network hydrogel described herein differs from previous hydrogels in at least the following ways: (1) mechanical strength, e.g., strong MNs patch provided herein withstanding a compressive stress value of 76.8 N (0.64 N/needle) which substantiates the MNs to penetrate the skin effectively (FIG. 6C); (2) drug loading and release or timely release of drugs, e.g., a rapid release of doxorubicin (DOX) and lipopolysaccharide (LPS) observed in the first 4 hours followed by a steady release occurring by the degradation of MNs. Degradation of interpenetrating polymer networked (IPN) hydrogel-based MNs in phosphate buffered saline (PBS) medium is attributed to sodium-calcium exchange in the hydrogel that enhances swelling and disintegration of hydrogel for ease drug diffusion (FIGS. 10A and 10B); (3) steady transdermal drug release, e.g., the MNs absorbing water and swelling, recognized by a progressive structural loosening with time (FIG. 7); (4) separability of the disulfide crosslinked substrate of the MNs, e.g., an improved rate of disintegration of the disulfide linked IPN hydrogel, and separability of MNs by adjusting the concentration of disintegrating agents (FIGS. 8C and 8D); (5) biocompatibility of IPN hydrogel, e.g., viability of cells treated with either N,N-bisacryloylcystine (BISS) or N,N'-methylenebisacrylamide (MBAAm) crosslinked hydrogel being greater than 85% on CT-2A-Luc cells and 92.6% on NIH-3T3 cells, even at a high concentration (0.1 g/mL), suggesting that the hydrogels are biocompatible and will not affect cells during transdermal drug delivery; (6) doxorubicin loaded MNs treating cancer cells with a higher $IC_{50}$ value or exhibiting better cell viability at the same concentration of DOX (FIGS. 11A and 11B); (7) a synergistic effect on tumor growth inhibition, e.g., the tumor growth on mice treated with dual drugs (LPS and DOX loaded MNs) being inhibited more than the one treated with DOX-only loaded MNs (FIGS. 12A to 12D); and (8) traversing the stratum corneum, conveying LPS to the immune-cell-rich epidermis, and eliciting a wide range of immune responses such as apoptosis, e.g., cancer cells undergoing apoptosis in response to drugs (LPS and DOX loaded MNs) and progression of tumor being inhibited (FIGS. 13A and 13B).

The efficacies of the disclosure will be further illustrated by following examples which are not intended to restrict the scope of the disclosure.

EXAMPLES

Example 1: Manufacture of IPN Hydrogel

Materials

Sodium alginate, sodium hydroxide (NaOH), [2-(methacryloyloxy)ethyl] dimethyl-(3-sulfopropyl) ammonium hydroxide (SBMA, 95%), α-ketoglutaric acid, acryloyl chloride (97%), calcium formate ($Ca(HCOO)_2$), L-cystine (≥99.7%), ethylenediaminetetraacetic acid (EDTA, ≥98.5%), D,L-dithiothreitol (DTT, ≥99%), methylthiazolyl-diphenyl-tetrazolium bromide (MTT, ≥97.5%), doxorubicin (DOX), and lipopolysaccharide (LPS) were purchased from Sigma Aldrich while N,N'-methylenebisacrylamide (MBAAm, 99.5%) was purchased from J. T. Baker. Phosphate buffered saline (PBS), Dulbecco's modified Eagle's medium (DMEM) and its supplements were obtained from Hyclone.

Synthesis of Disulfide Bond Crosslinking Agent

Disulfide crosslinker, N,N-bisacryloylcystine (BISS) was used for preparing IPN hydrogel as a separable substrate of the MNs. 2.7 g (11.2 mM) of L-cystine and 2 g (50 mM) of sodium hydroxide (NaOH) were dissolved in 70 mL of methanol at 0° C. in ice bath. When a clear and colorless solution was formed, 2.2 mL (27.2 mM) of acryloyl chloride was added dropwise, and the reaction was carried out by stirring for 4 hours at room temperature. Finally, the reaction mixture was purified through adding drop by drop into vigorously stirred cold ether, and the precipitate was separated by centrifuging. The residual ether was removed by drying in a vacuum oven for 12 hours. The successful synthesis of BISS was verified by Proton Nuclear Magnetic Resonance Spectroscopy ($^1$HNMR, Bruker AVANCE 600 MHz), Raman spectroscopy (JASCO NRS-5100 Laser) and Fourier-transform infrared spectroscopy (FT-IR, Thermo Nicolet 6700 system).

Preparation of MBAAm Crosslinked Pre-Gel Hydrogel Solution

Prior to formation of sequential interpenetrating polymer networked (IPN) hydrogel by chemical and ionic interaction, N,N'-methylenebisacrylamide (MBAAm) crosslinked pre-gel hydrogel solution was prepared as follows. First, 0.6984 g (500 mM) sulfobetaine methacrylate (SBMA) monomer was dissolved in 5 mL deionized (DI) water, and then 3.8 mg (5 mM) of MBAAm, a cross-linking agent, was added. After completely dissolved by stirring with a magnetic stirrer, 3.6 mg (5 mM) of α-ketoglutaric acid, a photo-initiator, was added and stirred under light protection. When the powder is completely dissolved, 0.5 g sodium alginate was added and stirred overnight to obtain a uniformly dissolved, slightly yellow viscous solution (MBAAm pre-gel hydrogel solution). Similarly, BISS crosslinked pre-gel hydrogel solution was prepared for a separable substrate of the MNs. Herein, instead of 5 mM MBAAm crosslinker, 50 mM of disulfide bond crosslinking agent (BISS) was used.

Fabrication of IPN Hydrogel-Based Separable MNs

The IPN hydrogel adopted sequentially of chemical crosslinking of SBMA network followed by ionic crosslinking of alginate network with calcium ions for fabricating relatively tough MNs arrays, as shown in FIG. 1A. The size, shape and arrangement of MNs were maintained by casting in a commercially available microneedle mold (Blueacre Technology, PDMS Mold at 600 μm height, 11×11 array) and centrifuged with a microplate centrifuge.

Figure 1B:
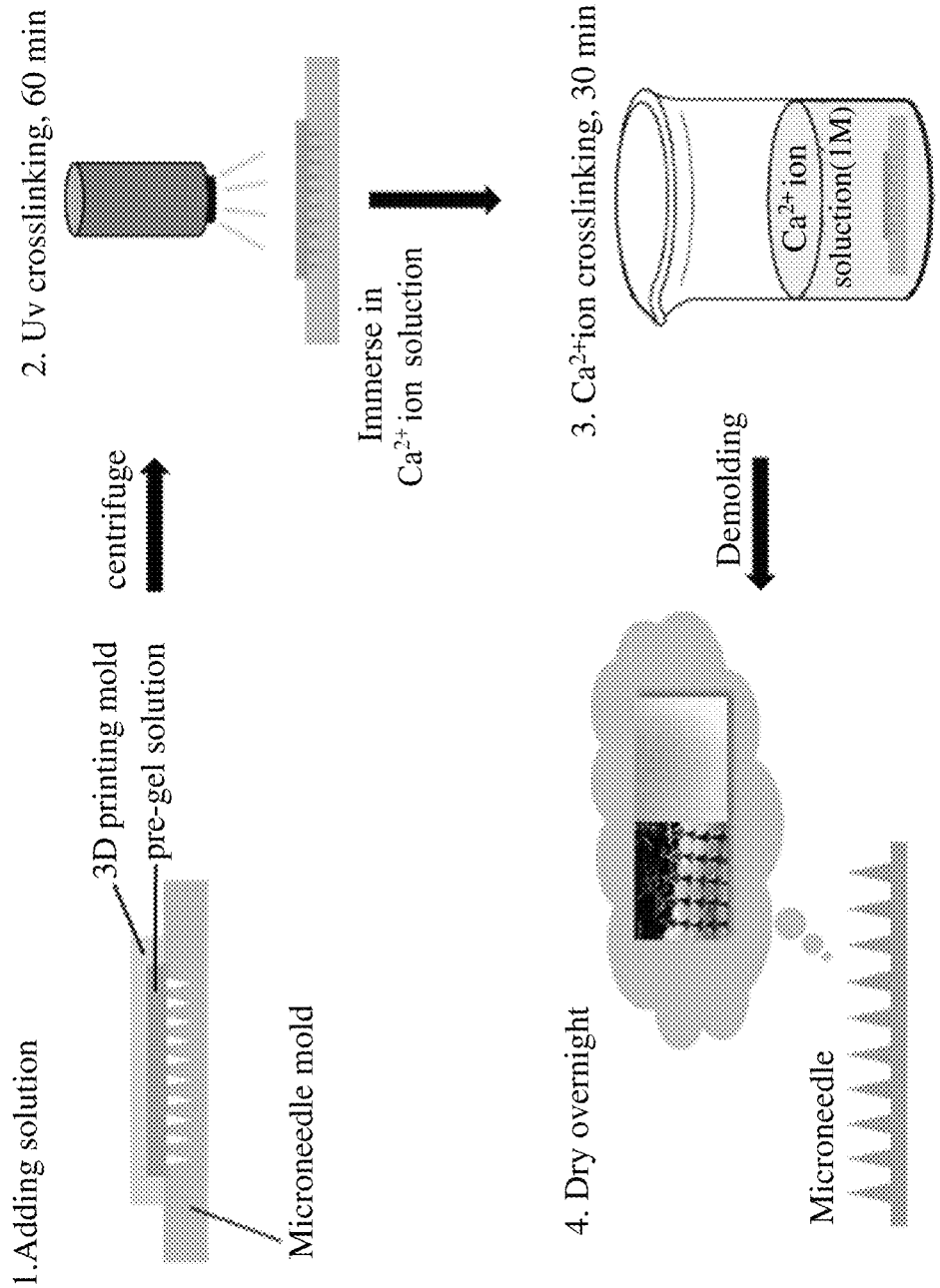
FIG. 1B is a schematic diagram showing the microneedle fabrication.

In brief, 0.5 mL of MBAAm pre-gel hydrogel solution was added into a microneedle mold and tightly covered with a 3D printing mold (thermoplastic polyurethane (TPU), 15 mm in length, 15 mm in width, and 3 mm in height) to prevent the solution from leaking out of the microneedle mold. Then, the mold was centrifuged at 1,500 rpm for 25 min followed by 3,000 rpm for 10 min to ensure complete filling of the solution into the microneedle mold and stack tightly on it. After centrifugation, the upper 3D printing mold was removed, and the upper layer of solution was scraped off (the base of the MNs). 0.5 mL of BISS pre-gel hydrogel solution was added on the top of the microneedle mold (the base of the MNs), covered with the 3D printing mold and centrifuged at 1,500 rpm for 30 min. Then, the pre-gel solution in the microneedle mold was photo-crosslinked by irradiating with a full-wavelength fiber optic light source for 60 minutes followed by ionic crosslinking by immersing in 1 M calcium ion aqueous solution (calcium formate) for 30 min. Afterwards, it was placed in the air for 24 h to evaporate water, and the completely dried separable MNs with a desired shape was peeled out from the mold. The process is shown in the schematic figure shown in FIG. 1B.

Example 2: Characterization of IPN Hydrogel

The formation of IPN hydrogel was characterized using Raman spectroscopy and FT-IR. For Raman spectra analysis, a small amount of hydrogel sample was placed in a silicon wafer, and representative functional groups in the polymer were detected by scanning the Raman spectra between 300 and 3,000 $cm^{-1}$. A piece of dried hydrogel sample was taken for FT-IR examination and verified with the formation of IPN hydrogel by comparing the characteristic signal shift of the monomers after polymerization.

Furthermore, the tensile test and compression test were performed using Universal Testing Machine (UTM) to investigate the mechanical properties of the hydrogel at different types of crosslinking, various molar ratios of the monomers, and different crosslinking time. The internal structure and surface morphology of IPN hydrogel and MNs were observed under Optical Microscope and Field-Emission Scanning Electron Microscope (FESEM, JSM 6500F, JEOL). Physical and chemical characteristics were evaluated as follows.

Swelling and Degradation of IPN Hydrogel

The prepared MNs were soaked in a PBS solution (pH 7.4) at 37° C. to evaluate the swelling rate of the hydrogel. After 30 min, 1 h, 2 h, 4 h, 8 h, 24 h and 48 h, the surface morphological changes of the MNs were observed with a digital electron microscope. Similarly, the separability of the disulfide bond crosslinked substrate of the MNs was evaluated by checking its rate of degradation under different concentrations of DTT and/or EDTA.

Skin Penetration Test

Figure 9B:
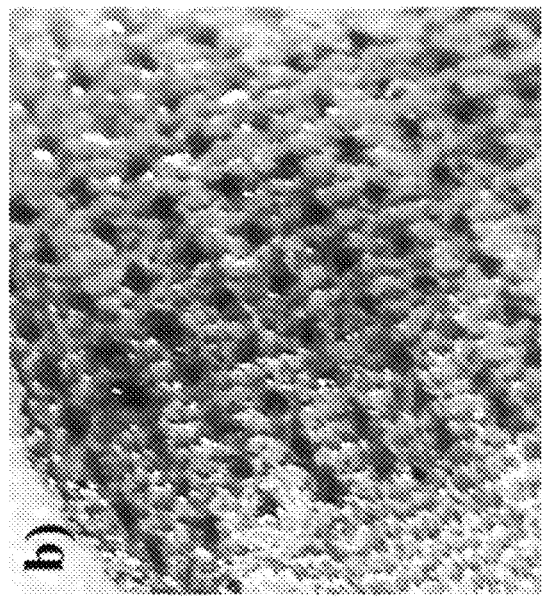
FIG. 9B is an optical image of round holes remained on the skin after MNs penetration.
Figure 9A:
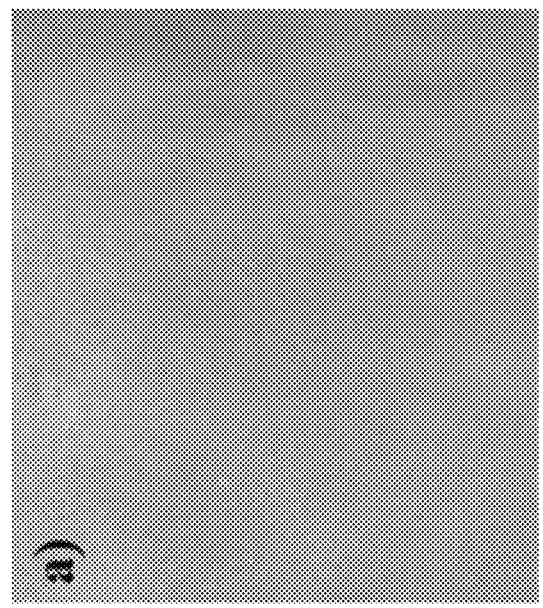
FIG. 9A is a photograph showing the mouse skin before penetration of the microneedle.
Figure 9D:
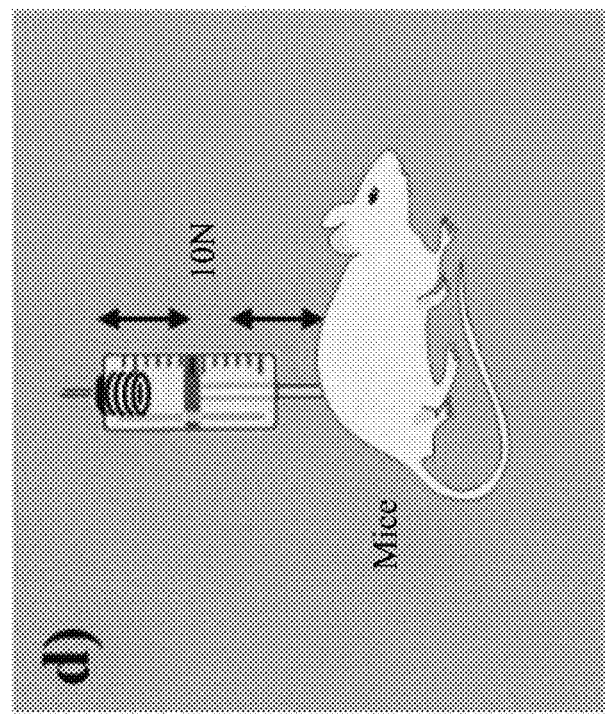
FIG. 9D is a schematic image of fixed force device during skin penetration test of a mouse

The skin penetration ability of the MNs array was examined using the skin of a C57BL/6 mouse with the guidelines of the Institutional Animal Care and Use Committee (IACUC-16-168). The mice were anesthetized by intramuscular injection of 0.15 mL anesthetic Zoletil 50 at a concentration of 10 mg/mL, and then the hairs from the back of the mouse where the MNs were applied were removed carefully using hair removal cream. Next, as shown in FIG. 9D, the MNs were fixed on the top of the mouse skin and pushed down by applying a vertical downward force of 10 N using a self-made pusher fixed force device to puncture the needle down the skin. Afterwards, the device and the MNs were removed, and the skin was stained with trypan blue to observe the punctures with a digital electron microscope. Furthermore, H&E staining of the skin was performed for detailed examination of the skin punctured by the MNs.

Drug Loading to the MNs

Doxorubicin (5 mg) and/or LPS (2 mg) was loaded into the gel by mixing with 5 mL of MBAAm pre-gel hydrogel solution during the preparation. The drugs were dissolved in 5 mL deionized water and mixed with SBMA monomer (0.6984 g, 500 mM), MBAAm crosslinker (3.8 mg, 5 mM), α-ketoglutaric acid (3.6 mg, 5 mM) and sodium alginate (0.5 g) sequentially and stirred overnight in the dark, and then drug loaded MNs (DOX loaded MNs, LPS loaded MNS and LPS/DOX loaded MNs) were fabricated using a microneedle mold with the same procedures of MNs preparation.

In Vitro Drug Release

Figure 14A:
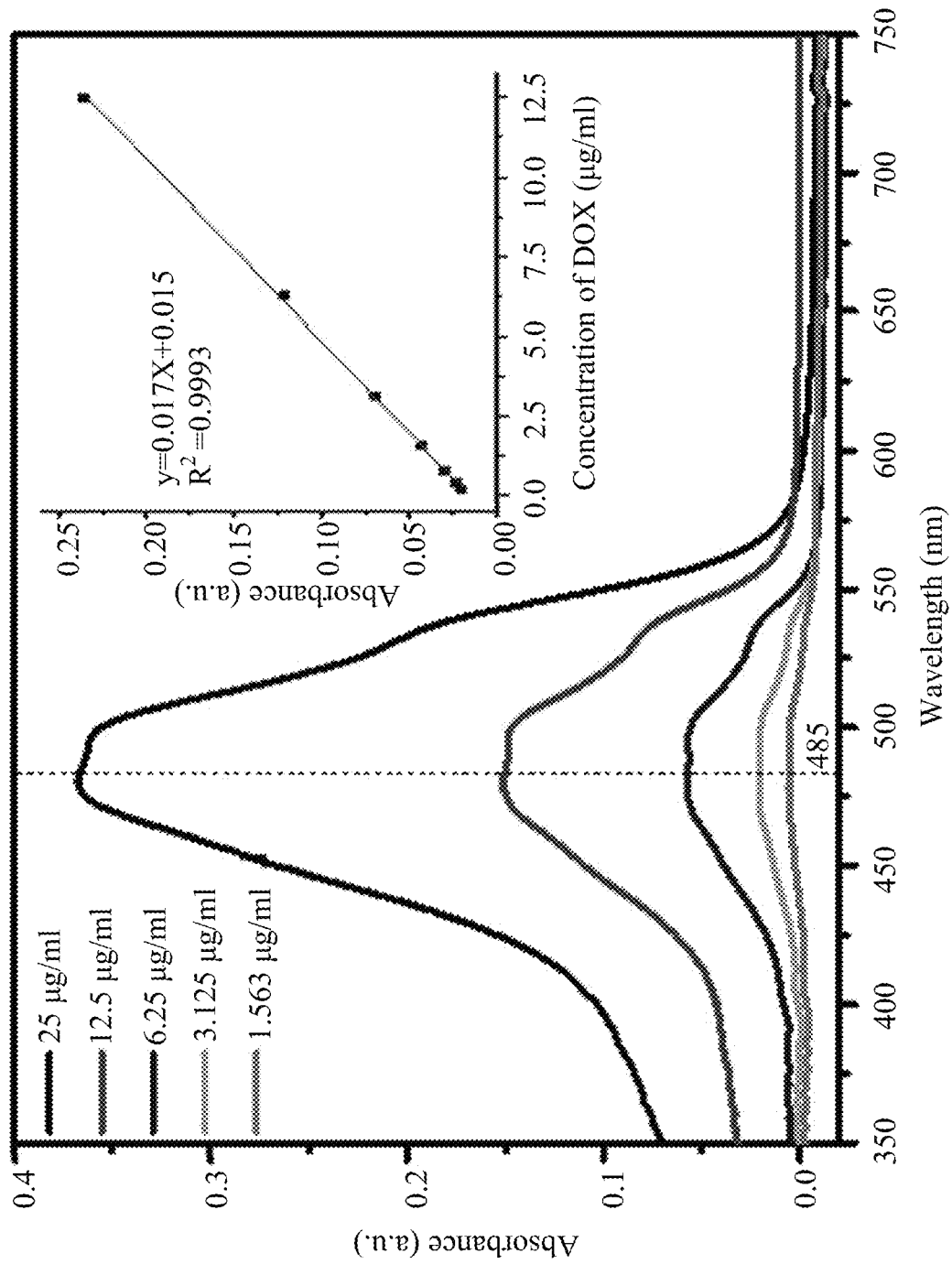
FIGS. 14A and 14B show Uv-vis absorption spectra at different serial concentrations and standard calibration curves of DOX and LPS, respectively.
Figure 14B:
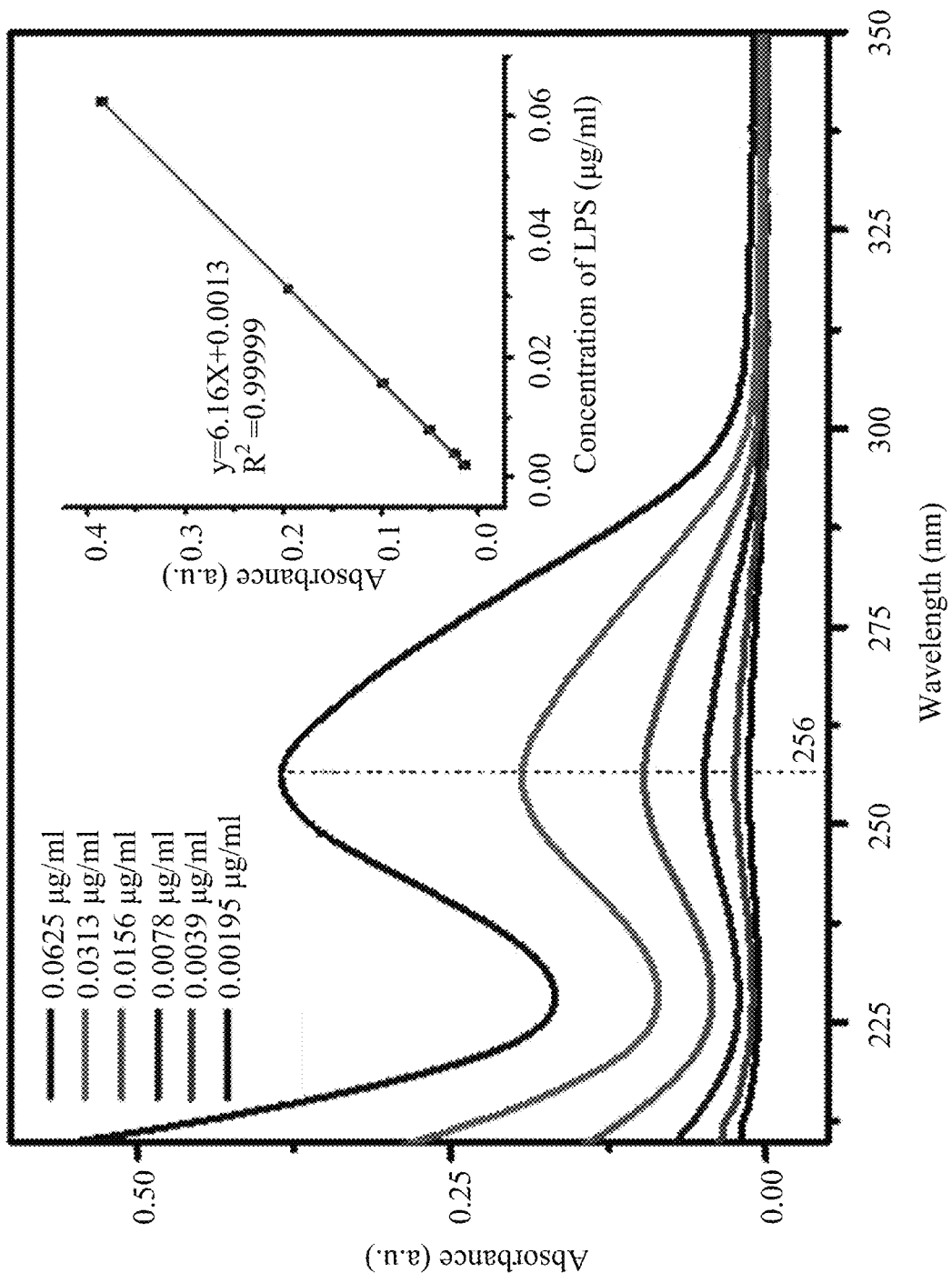

The drug-loaded MNs were soaked in 10 mL of PBS solution (pH 7.4) and put in a shaking incubator at 37° C. and 100 rpm to simulate the real drug release environment. About 2.5 mL of the release medium was withdrawn and replenished with an equivalent volume of PBS every half hour for the first 4 hours. Similarly, the released medium was collected at the 5th, 6th, 8th, 12th, and 24th hour followed by every 24 h for 7 days. Then, the cumulative drug released was determined by measuring the UV-Vis absorbance of DOX and LPS at 485 nm and 256 nm, respectively, and then calculated using the standard calibration curve of the free drugs, as shown in FIGS. 14A and B.

Biocompatibility

The biocompatibility of the hydrogel was examined by MTT assay using mouse glioma cancer cells (CT-2A-Luc cells) and mouse embryonic fibroblasts (NIH-3T3 cells) as model cell lines. To start with, the cells were cultured in a T-75 culture flask with a complete culture medium including DMEM (90%), fetal bovine serum (FBS) (10%), and antibiotic (1%) at 37° C. and 5% $CO_2$ incubator. When the confluence became 80% to 90%, the cells were sub-cultured into a 96-well plate at a density of $1\times10^4$ cells/well for 24 hours. Concurrently, the hydrogel samples were immersed in fresh medium within a centrifuge tube and incubated at 37° C. water bath for 24 hours. The concentration was set to 0.1 g/mL in accordance with ISO 10993-12. Then, the old medium of the cells in the 96-well plate was removed and washed with PBS, and the medium of the hydrogel sample was added to the cells followed by incubation for additional 24 h. Next, the old medium was replenished with 100 µL fresh medium containing 3-(4,5-dimethylthiazol-2-yl)-2,5-diphenyltetrazolium bromide (MTT) dye (1 mg/mL) and incubated for 4 hours. Then, MTT-containing medium was removed, and 100 µL of DMSO was added to dissolve the crystals, followed by incubation after 30 min. Afterwards, an ELISA micro-plate reader (Thermo Fisher Scientific, Waltham, USA) was used to read the absorbance of the sample at a wavelength of 570 nm (n=8) and estimate the percent of cell viability using the equation shown as below.

$$\textit{Celle viability}(\%) = \frac{\text{Absorbance of sample cells}}{\text{Absorbance of control cells}} \times 100$$

Animal Experiments

Seven-weeks-old female C57BL/6 mice were purchased from BioLASCO (Taiwan Co., Ltd.). All animal care and experimental procedures were carried out in compliance with the guidelines of the Institutional Animal Care and Use Committee (IACUC-16-168) in the National Defense Medical Center. The mice were housed in pathogen-free environment at 25±2° C. and 55±5% humidity under 12 h light-dark cycles and allowed free access to food and water. Then, after 1-week environmental acclimatization, CT-2A-Luc cells ($1.5\times10^6$ cells in 0.1 mL of medium) were inoculated subcutaneously into the right flank of each mouse and served as a developing tumor model. The mice were randomly divided into 5 groups (n=6 per group), and the tumor size was measured every 2 days with a digital caliper. When the subcutaneous tumor volume reached to about 30 to 50 $mm^3$ (about 10 days after injection), each group of mice was treated with different formulations of drug loaded MNs for a predetermined time period. Group 1 (control group): not treated; Group 2: treated with blank MNs; Group 3: treated with LPS loaded MNs; Group 4: treated with DOX loaded MNs; and Group 5: treated with LPS/DOX loaded MNs at an equivalent concentration of 5 mg/kg LPS and 10 mg/kg DOX. The drug loaded MNs were pasted on the subcutaneous tumor, and the separable substrate of the MNs was removed within 24 h using DTT (60 mM) and EDTA (300 mM) solution. During the entire experimental period (18 days), the tumor size and body weight were measured and recorded every 2 days for evaluating the antitumor efficacy or tumor growth inhibition rate in different treatment groups. The tumor volume (V) and tumor growth inhibition rate were calculated using the following equations (1) and (2), respectively.

$$\text{Tumor volume } (V) = \frac{W^2 \times L}{2} \quad (1)$$

$$\text{Tumor growth inhibition rate } (\%) = \frac{Vc - Vt}{Vc} \times 100 \quad (2)$$

In the equations, W and L refer to the shortest and longest tumor diameters, respectively, while Vc and Vt represent the mean tumor volume of the control group and the treatment groups, respectively, at the end of treatment.

Finally, the mice were sacrificed by cervical dislocation, and spleen and tumor tissues in each group were collected, fixed in 4% (w/v) PBS buffered paraformaldehyde as per the protocol of Darge 2021. Then, tissue staining and immunohistocompatibility analyses were conducted by experts at Toson Technology Co., Ltd., Taiwan.

Statistical Analysis

Each measurement was repeated at least three times, and the values were reported as mean±standard deviation. The statistical analysis of variances among groups was performed using two tailed student t-test, and P<0.05 was considered as statistically significant. Asterisks denoted a statistical significance (* P<0.05,  P<0.01, and * P<0.001)

Synthesis and Characterization of Disulfide Crosslinking Agent

N,N-bisacryloylcystine (BISS) disulfide bond crosslinking agent was synthesized to prepare a separable substrate of the MNs which can be easily removed from the MNs array and minimized discomforts on the MNs users. After the MNs were squeezed into the skin, the disulfide bond crosslinking the polymers forming the substrate of the MNs was dissolved by a reducing agent (e.g., DTT) that cleaves the disulfide bonds or by a chelating agent (e.g., EDTA) that chelates Ca' ions in alginate networks of the hydrogel. Therefore, the separable substrate of the MNs is easily disintegrated and removed with a reducing agent or a metal chelator, while the MNs arrays remained inside the skin for sustained transdermal release of drugs.

Figure 2A:
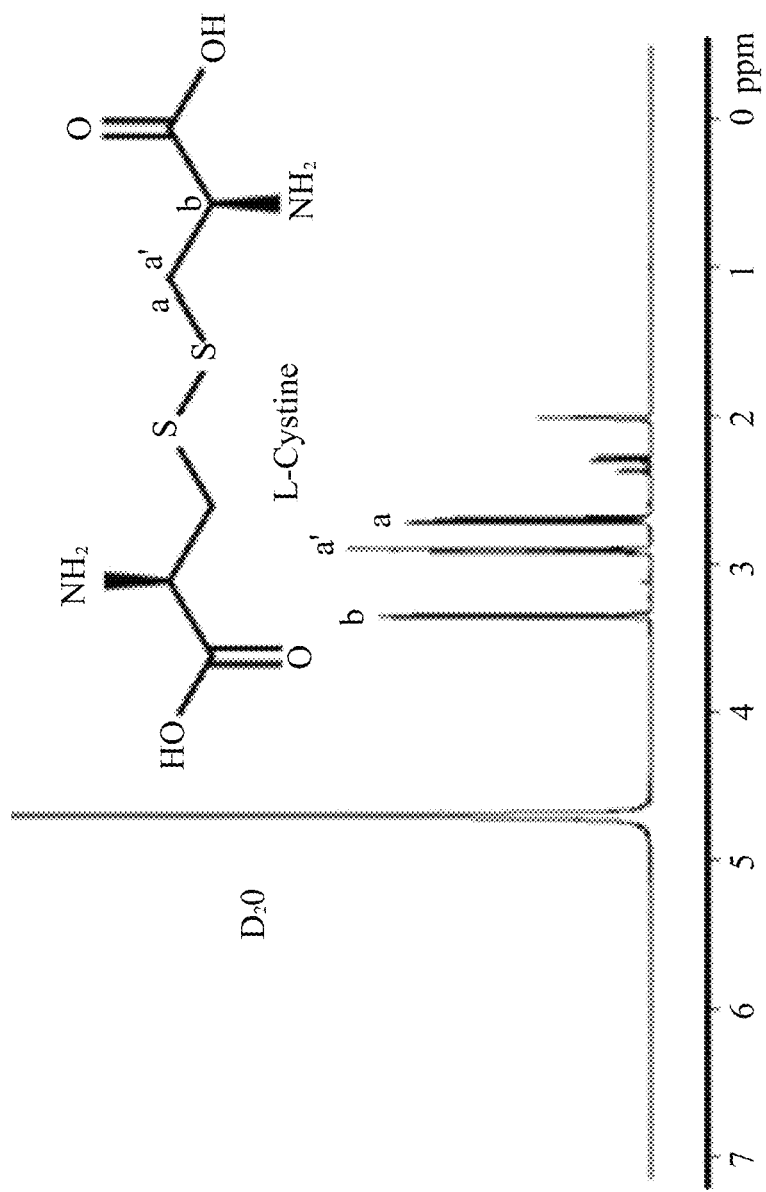
FIG. 2A is NMR and Raman spectroscopy analysis of disulfide crosslinking agent, BISS, and L-cystine monomer with the characteristic peaks of monomers, δ=2.89 to 3.01 ppm (a, a') and δ=3.48 ppm (b).
Figure 2B:
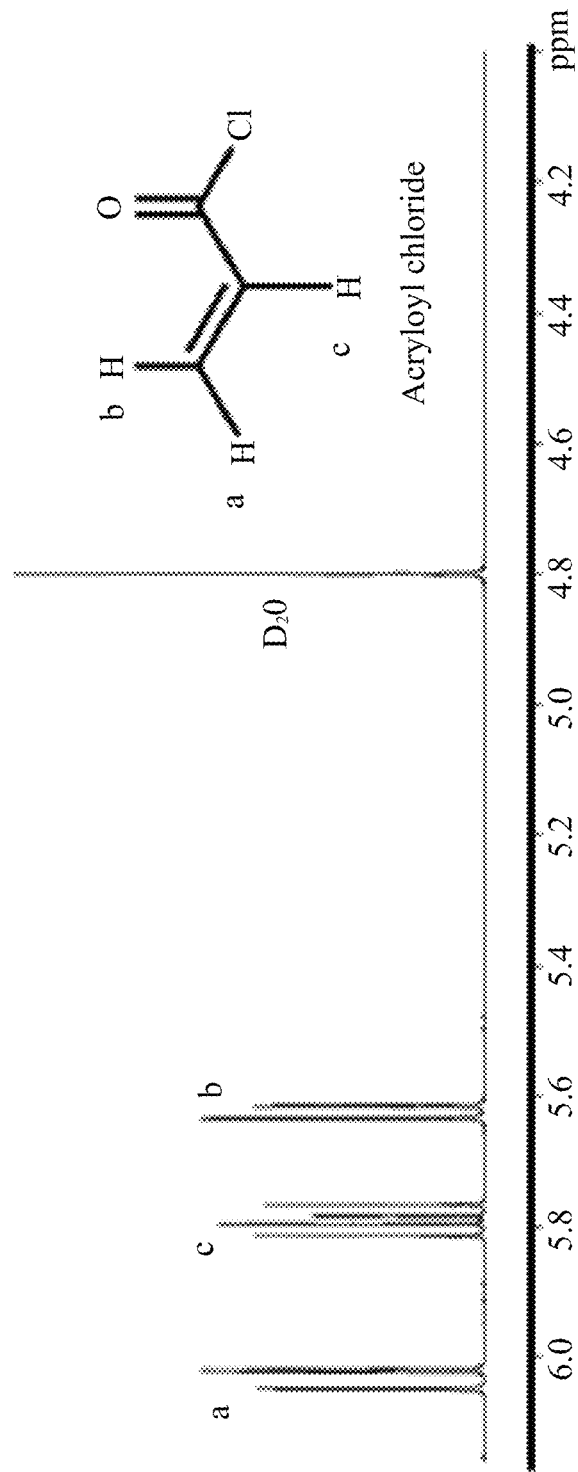
FIG. 2B shows the NMR and Raman spectroscopy analysis of disulfide crosslinking agent, BISS, and acryloyl chloride monomer with the characteristic peaks of monomers, δ=5.62 ppm (b), δ=5.80 ppm (c) and δ=6.14 ppm (a), used for the synthesis of BISS.
Figure 2C:
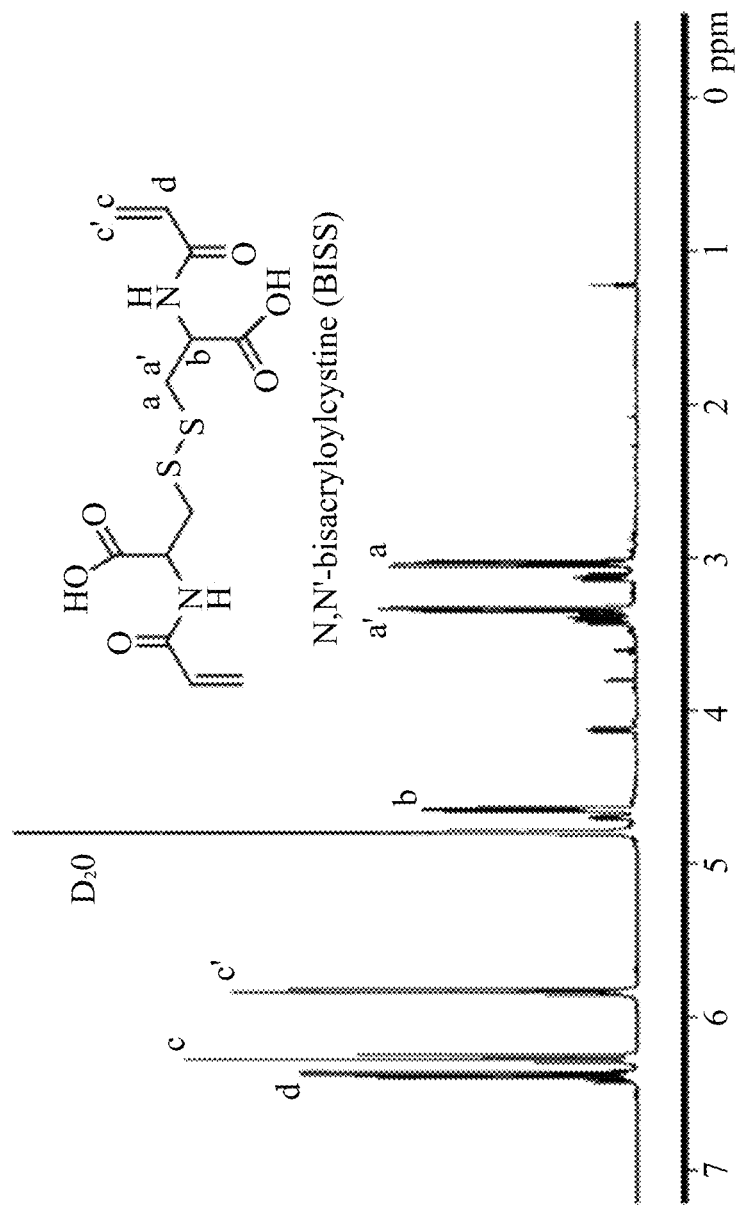
FIG. 2C is NMR and Raman spectroscopy analysis of disulfide crosslinking agent, BISS, with the corresponding proton spectra appeared at δ=3.05 ppm (a) and 3.4 ppm (a'), δ=4.8 ppm (b), δ=5.85 ppm (c), 6.3 ppm (c') and δ=6.45 ppm (d) that verified the successful synthesis of the disulfide bond crosslinking agent (BISS).

The successful preparation of disulfide crosslinker (BISS) was first confirmed using $^1$HNMR. As shown in FIG. 2C, the corresponding proton spectra appeared at δ=3.05 ppm (a) and 3.4 ppm (a'), δ=4.8 ppm (b), δ=5.85 ppm (c) and 6.3 ppm (c') and δ=6.45 ppm (d) verified the successful synthesis of the disulfide bond crosslinking agent (BISS). FIGS. 2A and 2B also showed the characteristic peaks of the monomers. As shown in FIG. 2A, the signals at δ=2.89 and 3.01 ppm (a, a') and δ=3.48 ppm (b) referred to the methylene and methine proton of L-cystine, respectively. Similarly, as shown in FIG. 2B, the spectra at δ=5.62 ppm (b), δ=5.80 ppm (c) and δ=6.14 ppm (a) were the representative peaks of acryloyl chloride monomer used for the synthesis of BISS.

Figure 2D:
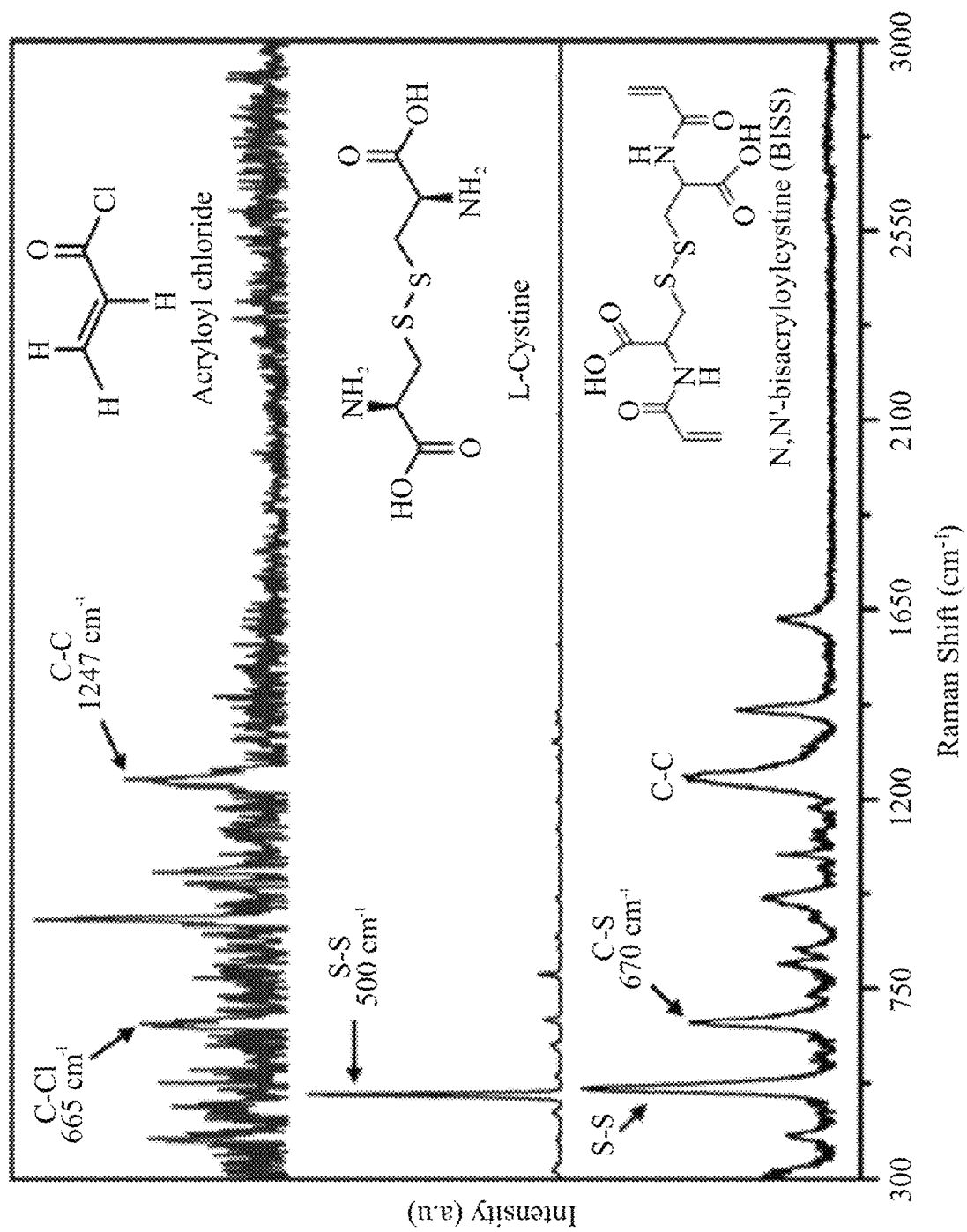
FIG. 2D is Raman spectroscopy to identify the covalent bonds formed in the disulfide cross-linking agent (BISS) and the characteristic Raman signals at 500 cm−1, 670 cm−1, and 1247 cm−1 in BISS represented the S—S, C—S and C—C bonds, respectively, indicating the successful synthesis of the crosslinker.

The Raman spectroscopy was also employed to identify the covalent bonds formed in the disulfide cross-linking agent (BISS). Evidently, as shown in FIG. 2D, the characteristic Raman signals at 500 cm$^{-1}$, 670 cm$^{-1}$, and 1247 cm$^{-1}$ in BISS represented the S—S, C—S and C—C bonds, respectively, indicating the successful synthesis of the crosslinker.

Figure 15:
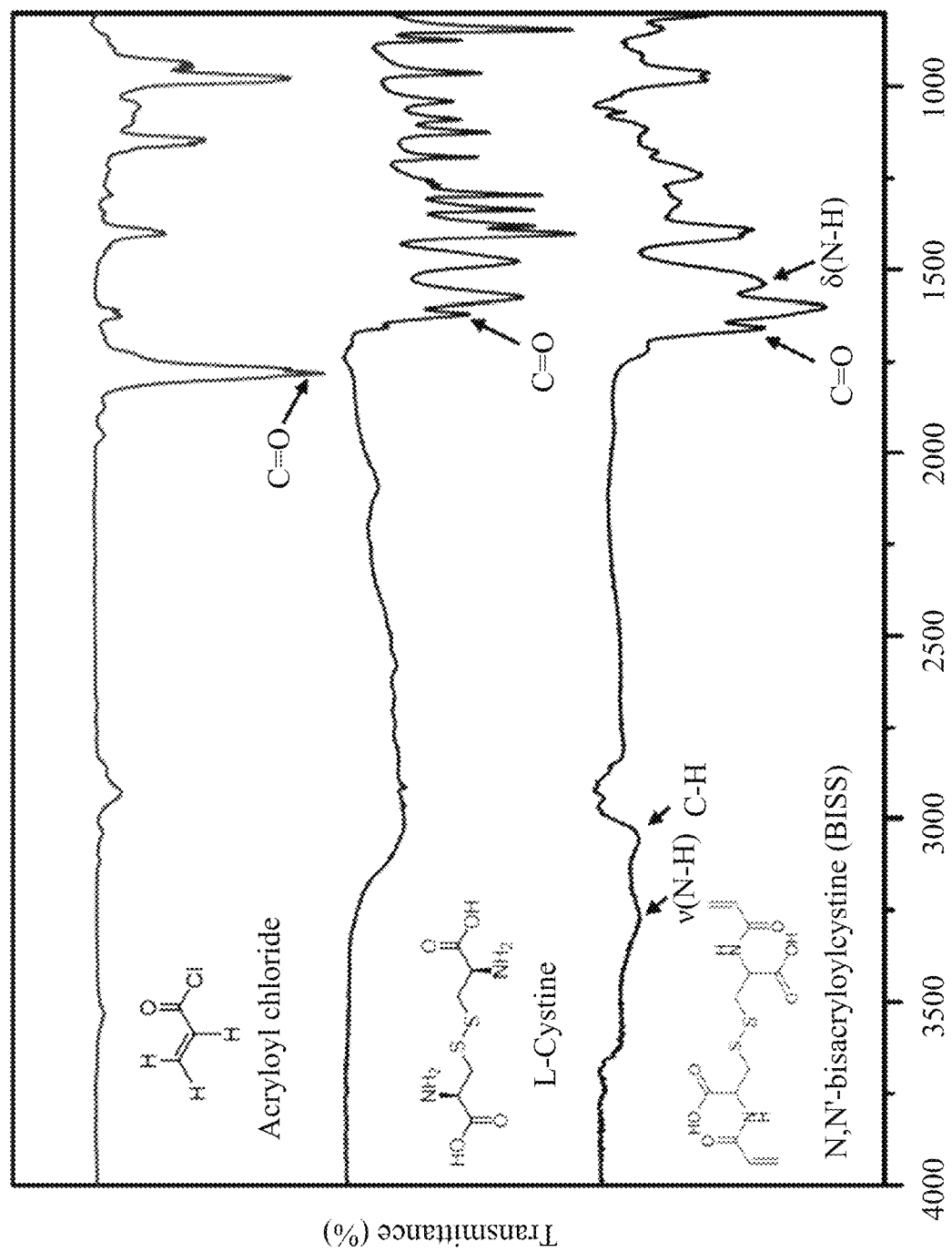
FIG. 15 shows the FTIR spectrum of disulfide bond crosslinker (BISS) and its monomers

Moreover, as shown in FIG. 15, the FT-IR result further proved the successful synthesis of BISS. A characteristic shifting of a vibration signal of C=O bond to 1703 cm$^{-1}$ in BISS from 1810 cm$^{-1}$ in acryloyl chloride and 1680 cm$^{-1}$ in L-cystine was an indicator for the formation of the cross-linking agent.

Example 3: Characterization of IPN Hydrogel

Figure 3A:
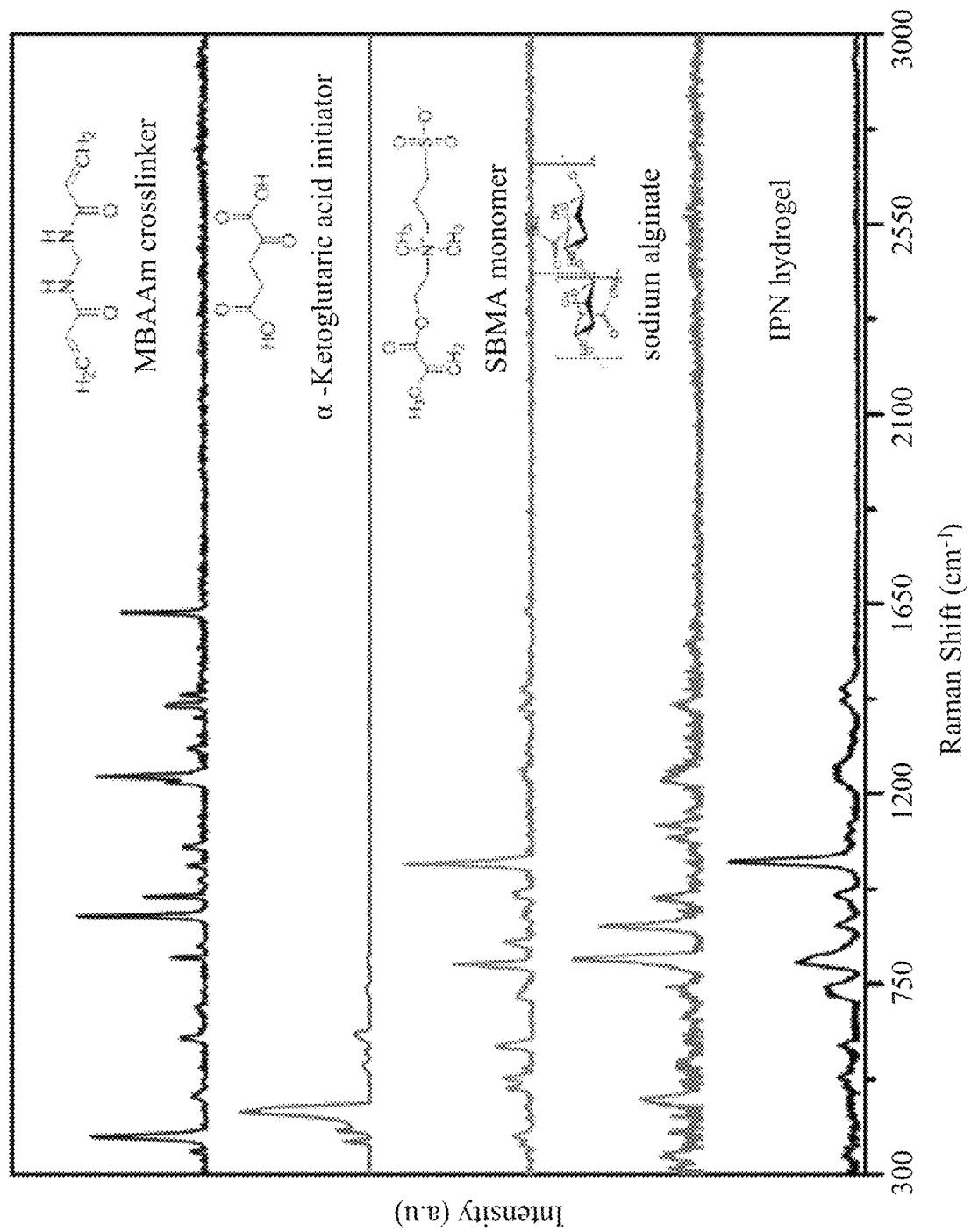
FIG. 3A is Raman spectrum showing the Raman signal of IPN hydrogel appeared at about 1133 $cm^{-1}$, representing the asymmetrical vibration of $SO_3^-$ derived from SBMA. The characteristic peaks at 807 $cm^{-1}$, 888 $cm^{-1}$, and 954 $cm^{-1}$ represent the stretching vibration of C—C, C—O, and C—C—O from sodium alginate, respectively. Raman signals at 1240 $cm^{-1}$ and 1413 $cm^{-1}$ representing the stretching vibrations of $COO^-$ of alginate confirmed the formation of IPN hydrogel. The characteristic Raman spectra of MBAAm crosslinking agent and photo-initiator (α-ketoglutaric acid) are not visible in IPN hydrogel, suggesting that the toxic monomers were completely reacted for the formation of IPN hydrogel, and the possible pernicious effect of the hydrogel would be negligible.

The successful preparation of IPN through a sequential free radical polymerization of SBMA (chemical crosslinking) followed by ionic crosslinking of sodium alginate with calcium ions was confirmed using Raman spectroscopy and FT-IR. As shown in FIG. 3A, the Raman signal of IPN hydrogel appeared at about 1133 cm$^{-1}$, indicating the asymmetrical vibration of $SO^{3-}$ derived from SBMA. Similarly, the characteristic peaks at 807 cm$^{-1}$, 888 cm$^{-1}$, and 954 cm$^{-1}$ designated for stretching vibration of C—C, C—O, and C—C—O from sodium alginate, respectively, were observed. Additionally, Raman signals at 1240 cm$^{-1}$ and 1413 cm$^{-1}$ represented the stretching vibrations of COO— of alginate confirmed the formation of IPN hydrogel. Obviously, the characteristic Raman spectra of MBAAm crosslinking agent and photo-initiator (α-ketoglutaric acid) were not visible in IPN hydrogel, suggesting that the toxic monomers were completely reacted for the formation of IPN hydrogel, and the possible pernicious effect of the hydrogel would be negligible.

Figure 3B:
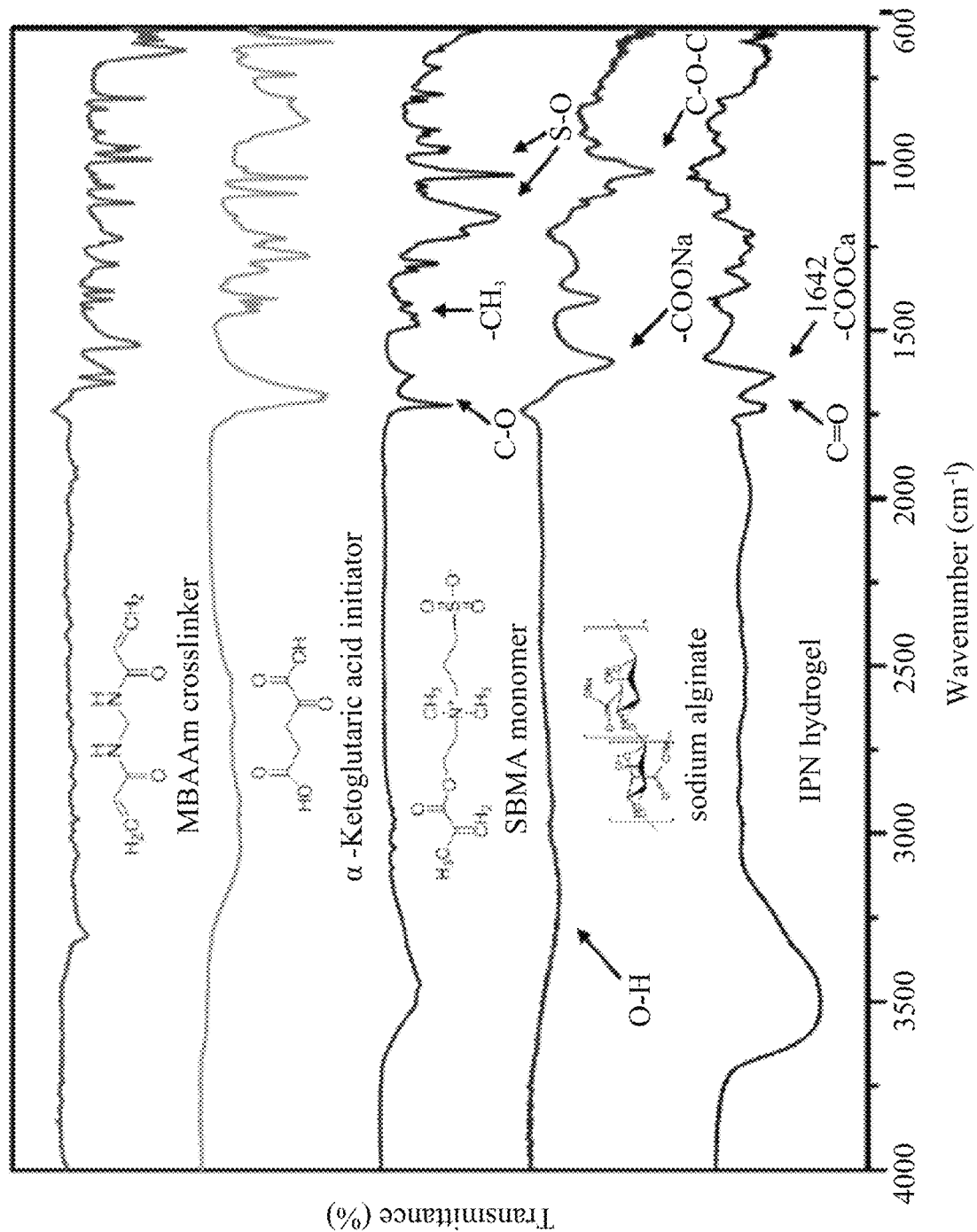
FIG. 3B is FT-IR spectrum of the chemical shifting of $COO^-$ signal from 1595 $cm^{-1}$ in sodium alginate to 1642 $cm^{-1}$ in IPN hydrogel, conveying the formation of ionic crosslinking with calcium ions (—COOCa).

The IPN hydrogel was further characterized using FT-IR spectroscopy which can be used to detect the functional groups of the polymers before and after polymerization. As shown in FIG. 3B, the chemical shifting of COO signal from 1595 cm$^{-1}$ in sodium alginate to 1642 cm$^{-1}$ in IPN hydrogel conveyed the formation of ionic crosslinking with calcium ions (—COOCa). Moreover, a sharp signal appeared at 1720 cm$^{-1}$ of the IPN hydrogel was due to the vibration of C=O of SBMA monomer which clearly proved the chemical crosslinking of the hydrogel. The disappearance of the representative FT-IR signals of the photo-initiator and MBAAm crosslinker after polymerization also further confirmed the formation of IPN hydrogel.

Morphology of INP Hydrogel

The internal structure of the IPN hydrogel formed by crosslinking with different molar ratios of SBMA monomer and sodium alginate were examined by field-emission scanning electron microscope (FESEM). Keeping other parameters constant (60 min photo-crosslinking with MBAAm and 30 min ionic crosslinking with 1 M $Ca^{2+}$), the molar ratio of SBMA:alginate was increased from 1:1 to 2:1, and to 3:1 by reacting 0.5 M, 0.67 M and 0.75 M SBMA with 0.5 M, 0.33 M and 0.25 M sodium alginate, respectively.

Figures 4A, 4B, 4C:
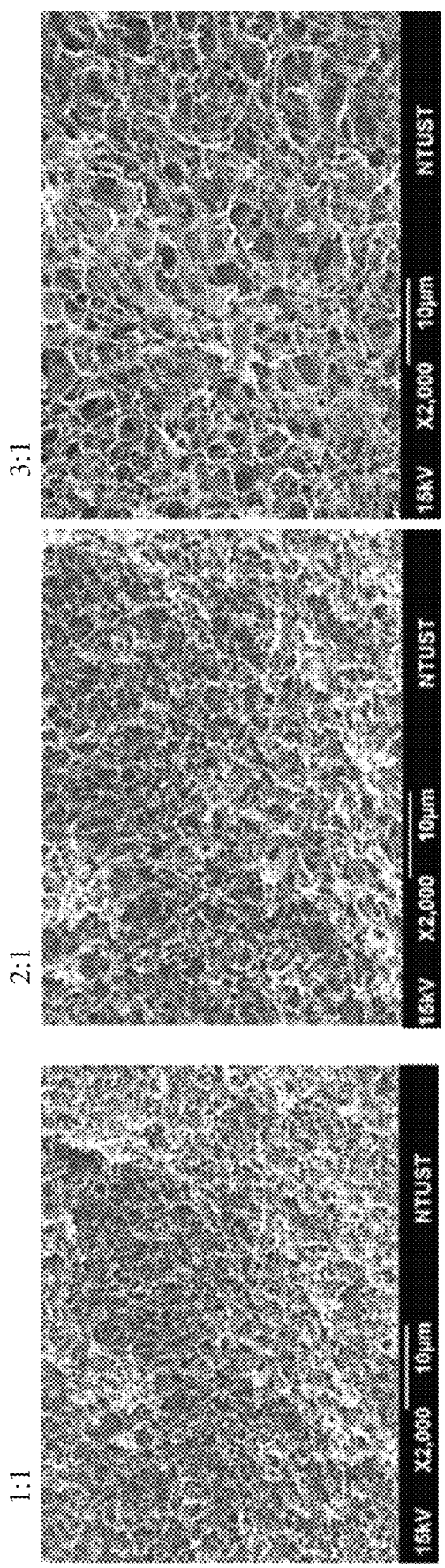
FIGS. 4A to 4C are a series of FESEM images of the internal structure of the IPN hydrogel with SBMA:alginate monomer ratios of 1:1, 2:1, and 3:1, respectively.

The FESEM image of the IPN hydrogel showed the porous structure, which was mainly due to the polymerization of SBMA. As shown in FIGS. 4A to 4C, the size of the internal pores of the hydrogel was increased with increased SBMA:alginate molar ratio. One of the possible reasons might be that at a fixed time period (60 min) of photo-polymerization, the number of SBMA monomers polymerized would be limited, and thus the crosslinking density of the hydrogel was decreased with the increased proportion of SBMA. Since the pore size of the IPN hydrogel is inversely proportional to the crosslinking density of the copolymers, it was observed that a relatively larger pore size is at the ratio of 3:1 (FIG. 4C). On the other hand, as the proportion of sodium alginate decreased, the ionic crosslinking density of the IPN hydrogel would be decreased, and its internal pores increased. However, a hydrogel with better mechanical properties is required to fabricate strong MNs for skin penetration, and a hydrogel formed with a higher crosslinking density (1:1 ratio) was selected for further experiments.

Figure 5C:
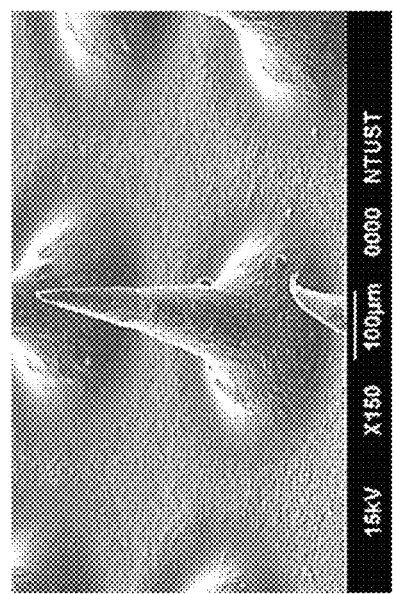
FIGS. 5B and 5C are FESEM images of MNs morphology.
Figure 5B:
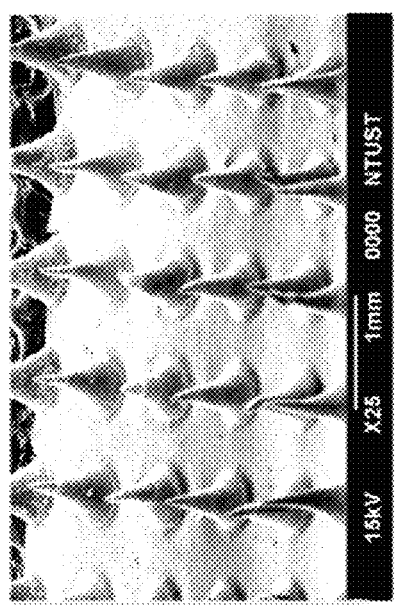
Figure 5A:
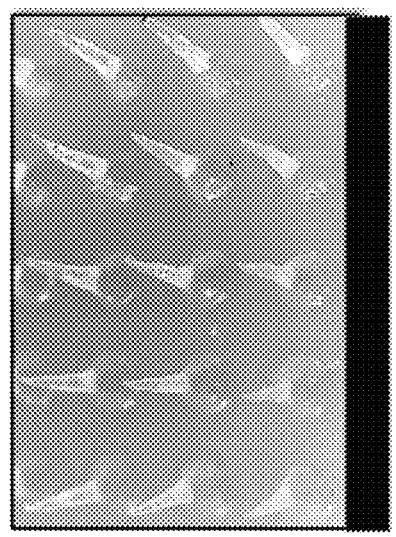
FIG. 5A is microscopic observation of MNs morphology.

Therefore, a 1:1 molar ratio of SBMA and alginate monomer was employed for MNs fabrication using a microneedle mold, and the shape of the MNs were confirmed using an optical microscope and FESEM imaging. As shown in FIGS. 5A to 5C, both the optical and FESEM images of dried MNs confirmed that a uniform size and shape of MNs arrays with specified arrangements were formed. The energy dispersive spectroscopy (EDS) analysis from FESEM imaging was also verified homogenous distribution of polymers across the MNs arrays. The tips of the MNs were reasonably long; for example, the needle height is at least 600 μm, with the needle base of at least 300 μm and with tip to tip of at least 600 μm and array number of at least 11×11=121. The tip of the MNs is sharp enough for penetrating into the epidermis of the skin.

TABLE 1

Specifications of microneedle array prepared by IPN hydrogel

| Specification | Needle height | Needle Base | Tip to tip | Array number |
|---|---|---|---|---|
| Measurement | 600 μm | 300 μm | 600 μm | 11 × 11 = 121 |

Mechanical Strength of INP Hydrogel

The mechanical properties of the IPN hydrogel at different conditions such as type of crosslinking (ionic crosslinking, photo-crosslinking, or combination of the two) and the molar ratio of monomers used for polymerization were investigated using Universal Testing Machine (UTM).

Figure 6A:
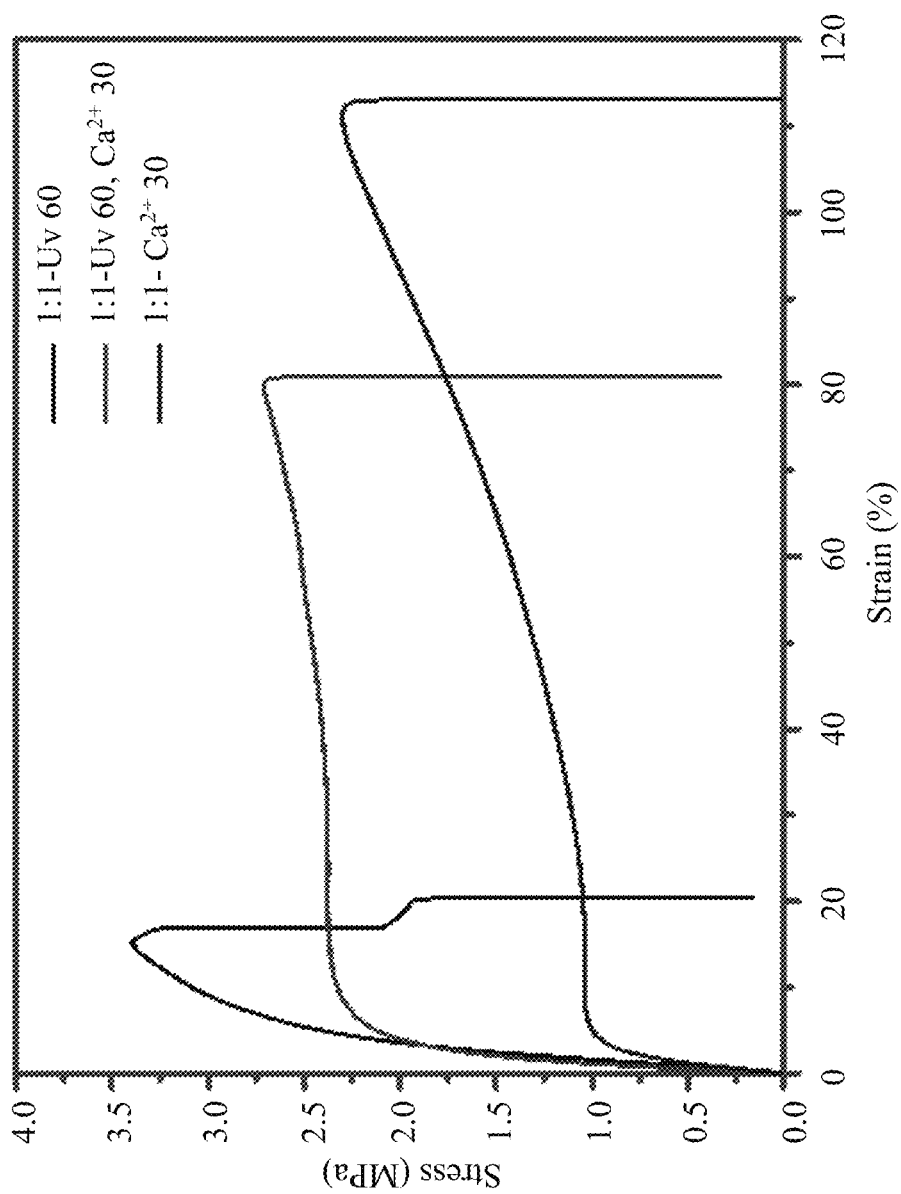
FIGS. 6A to 6C are line graphs showing the mechanical behavior of IPN hydrogel.

As depicted in FIG. 6A, and in Table 2 below, the mechanical properties of IPN hydrogel with different cross-linking methods were evaluated. Hydrogels formed by photo-crosslinking (Uv for 60 min) has the highest maximum tensile strength of 3.449 MPa than hydrogels formed by ionic crosslinking (1M $Ca^{2+}$ for 30 min) (2.302 MPa) or a sequential photo-ionic crosslinking (2.71 MPa). Nevertheless, its strain was low (20%) as compared with ionic cross linked (113%) or sequential photo-ionic crosslinked (80%) hydrogels. Herein, hydrogels formed by only chemically crosslinked networks exhibited extremely high mechanical structure with high tensile strength but brittle. On the contrary, hydrogels formed by only ionic cross linkage had the highest extension (strain=113%) but lowest tensile strength (stress=2.301 MPa), suggested that the physically crosslinked hydrogel had low mechanical strength with soft structure and prominent toughness. Essentially, the hydrogel formed by sequential photopolymerization (chemical cross linkage) followed by ionic interaction (physical cross linkage), exhibited an optimal tensile strength (2.71 MPa) and strain (81%) with highest Young's modulus (1.32 MPa) which is strong and stiff enough for needle penetration into the skin in the disclosure.

Figure 6B:
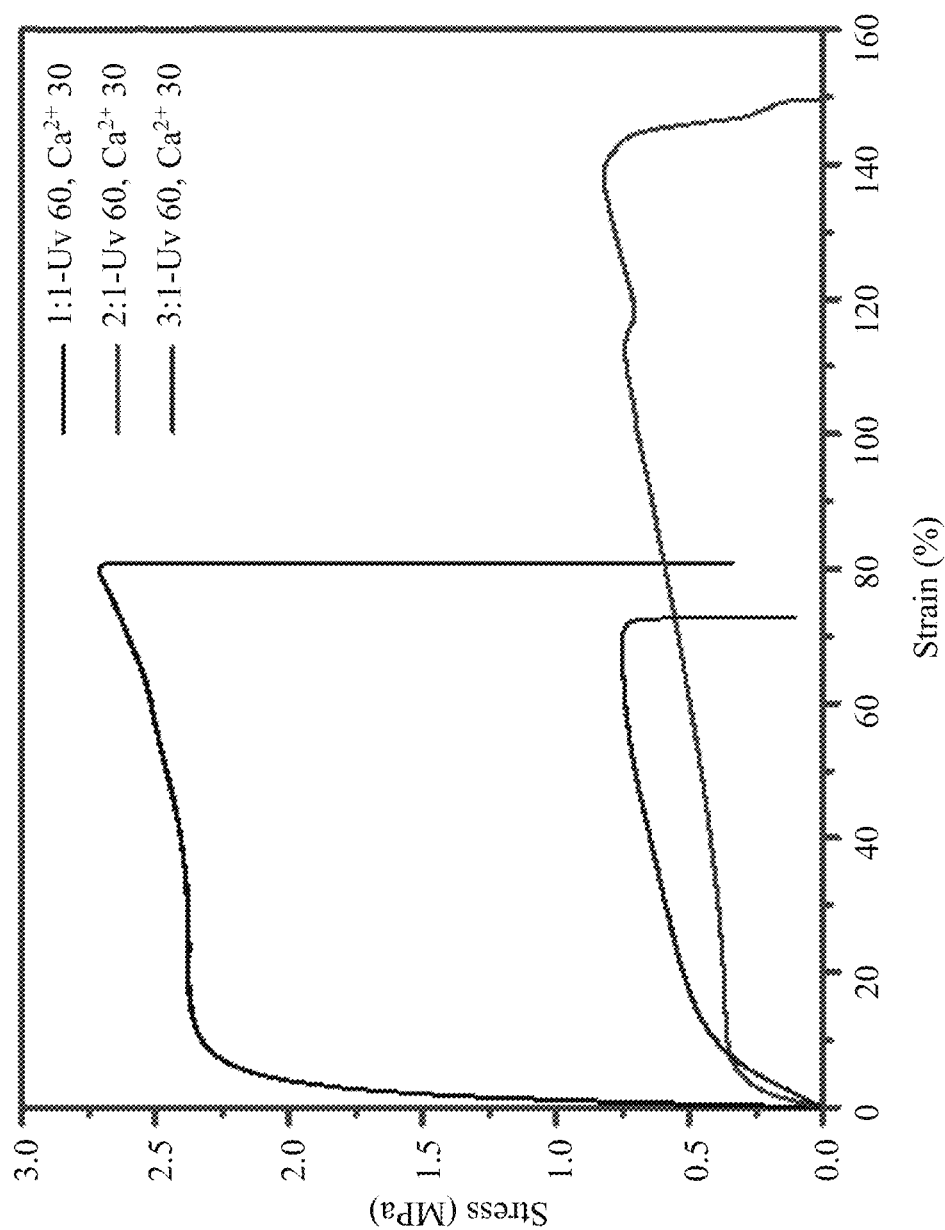

The mechanical properties of the IPN hydrogel was further examined at different molar ratio of SBMA and sodium alginate monomers (1:1, 2:1 and 3:1). The tensile tests in FIG. 6B depicted the mechanical strength and toughness of the IPN hydrogel gradually decreased with increasing the ratio of SBMA:sodium alginate from 1:1 to 2:1 and to 3:1, which was attributed to the density of crosslinking networks. As depicted in FIG. 4, in FESEM results of IPN hydrogel, the density of crosslinked networks decreased with increasing the proportion of SBMA to sodium alginate and subsequently the internal pore sizes were increased. As depicted in FIG. 6B and Table 2, a 1:1 molar ratio of the monomers has a better crosslinked network density and enabled to obtain hydrogel with relatively better mechanical strength (2.71 MPa maximum tensile strength, 81% strain and 1.31 MPa Young's modulus) in the disclosure. Generally, a sequential photo-crosslinking (60 min) followed by ionic crosslinking (1M $Ca^{2+}$ for 30 min) at 1:1 molar ratio of SBMA and sodium alginate resulted a dense IPN hydrogel with better mechanical strength while maintaining good ductility.

TABLE 2

Mechanical properties of IPN hydrogel at different cross-linking conditions and monomer ratios

| | Types of polymerization | Ultimate tensile strength (MPa) | Young's modulus (MPa) | Strain (%) |
|---|---|---|---|---|
| D/t cross-linking | 1:1-Uv 60 | 3.449 | 0.5095 | 20 |
| | 1:1-$Ca^{2+}$ 30 | 2.302 | 0.5595 | 113 |
| | 1:1-Uv 60, $Ca^{2+}$30 | 2.71 | 1.3106 | 81 |
| D/t molar ratio | 1:1-Uv 60, $Ca^{2+}$30 | 2.71 | 1.3106 | 81 |
| | 2:1-Uv 60, $Ca^{2+}$30 | 0.82 | 0.1706 | 149 |
| | 3:1-Uv 60, $Ca^{2+}$30 | 0.75 | 0.0531 | 72.7 |

1:1-Uv 60 = 1:1 molar ratio of SBMA and sodium alginate photopolymerized for 60 min.
1:1-$Ca^{2+}$30 = 1:1 molar ratio of SBMA and sodium alginate ionic crosslinked with $Ca^{2+}$(1M) for 30 min
D/t = different Moreover, as depicted in FIG. 6C, the MNs fabricated from IPN hydrogel at 1:1-Uv60, $Ca^{2+}$ 30 (i.e. 1:1 ratio of monomers and photo-cross linkage for 60 min followed by $Ca^{2+}$ ionic cross linkage for 30 min) formulation can withstand a compressive stress value of 76.8 N (0.64 N/needle), which substantiated the MNs to penetrate the skin effectively. This sequential double cross-linkage of the hydrogel provided a stronger MNs arrays than the MNs made from PLA/PLGA copolymer (~0.15 N/needle) (Li et al. Nat Biomed Eng 3(3) (2019) 220-229) and PVA/PVP copolymer (~0.17 N/needle) (Song et al. ACS Biomater Sci Eng 6(7) (2020) 4116-4125).

Swelling and Degradation Properties

The swelling behavior of the MNs were assessed by soaking it in PBS solution (pH 7.4) at 37° C. and observed the morphological changes under microscopic imaging. As shown in FIG. 7, the MNs absorbed water and swelled which was recognized by a progressive structural loosening with time. After 24 hours, the internal structure of IPN hydrogel was disintegrated and the shape of MNs were mostly collapsed. This swelling and subsequent collapsing of MNs structure attributed to the presence of sodium ions in the PBS solution which is an ion exchange reaction with the calcium alginate hydrogel networks. The calcium ion on the COO— group of alginates in the IPN hydrogel was gradually replaced by sodium ion and the electrostatic repulsive force on the COO— group increased. As a result, the interpenetrating networks of the hydrogel were gradually loosened and increased the swelling of the hydrogel followed by structural collapsing of the MNs. This is an essential phenomenon for steadily transdermal drug release from MNs.

Separability of the Disulfide Crosslinked Substrate of the MNs

The separability of the disulfide crosslinked substrate of the MNs was decided based on the rate of disintegration of disulfide crosslinked IPN hydrogel. The hydrogel was soaked in the reducing agent (DTT) and/or metal chelating agent (EDTA) solutions and the rate of disintegration of separable disulfide crosslinked IPN hydrogel was determined by measuring the remaining weight at different time interval for 1 hour. The rate of degradation was examined at different monomer:crosslinker ratios in a fixed concentration of disintegrating agents or keeping the monomer:crosslinker ratios in different concentration of disintegrating agents.

Figure 8A:
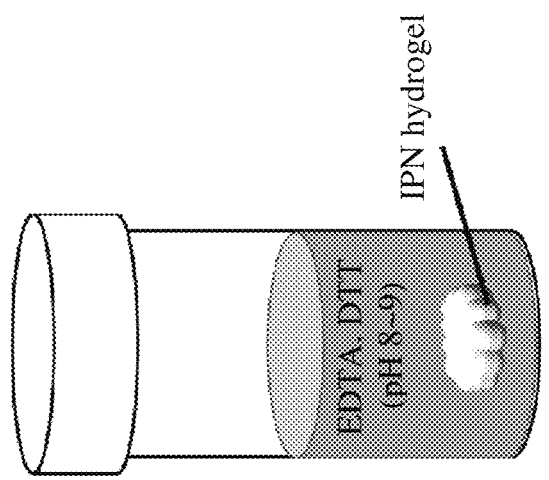
FIG. 8A is a schematic image of separable IPN hydrogel with crosslinker immersed in a mixture of DTT and EDTA solution (DTT 20 mM, EDTA 100 mM).
Figure 8B:
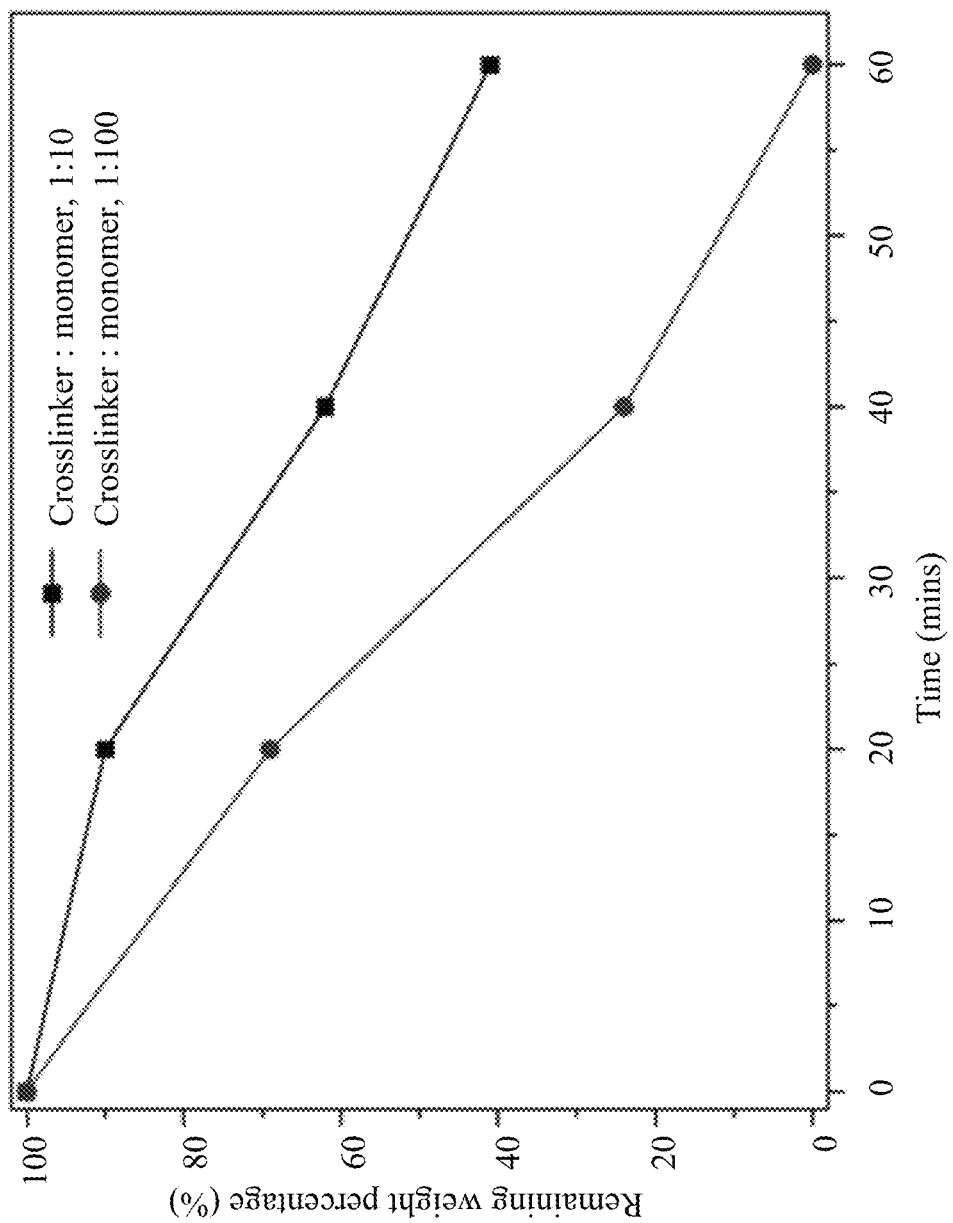
FIG. 8B is a line graph showing the effect of the concentration of crosslinker at a ratio of 1:10 and 1:100 on the rate of degradation of the separable IPN hydrogel.
Figure 8C:
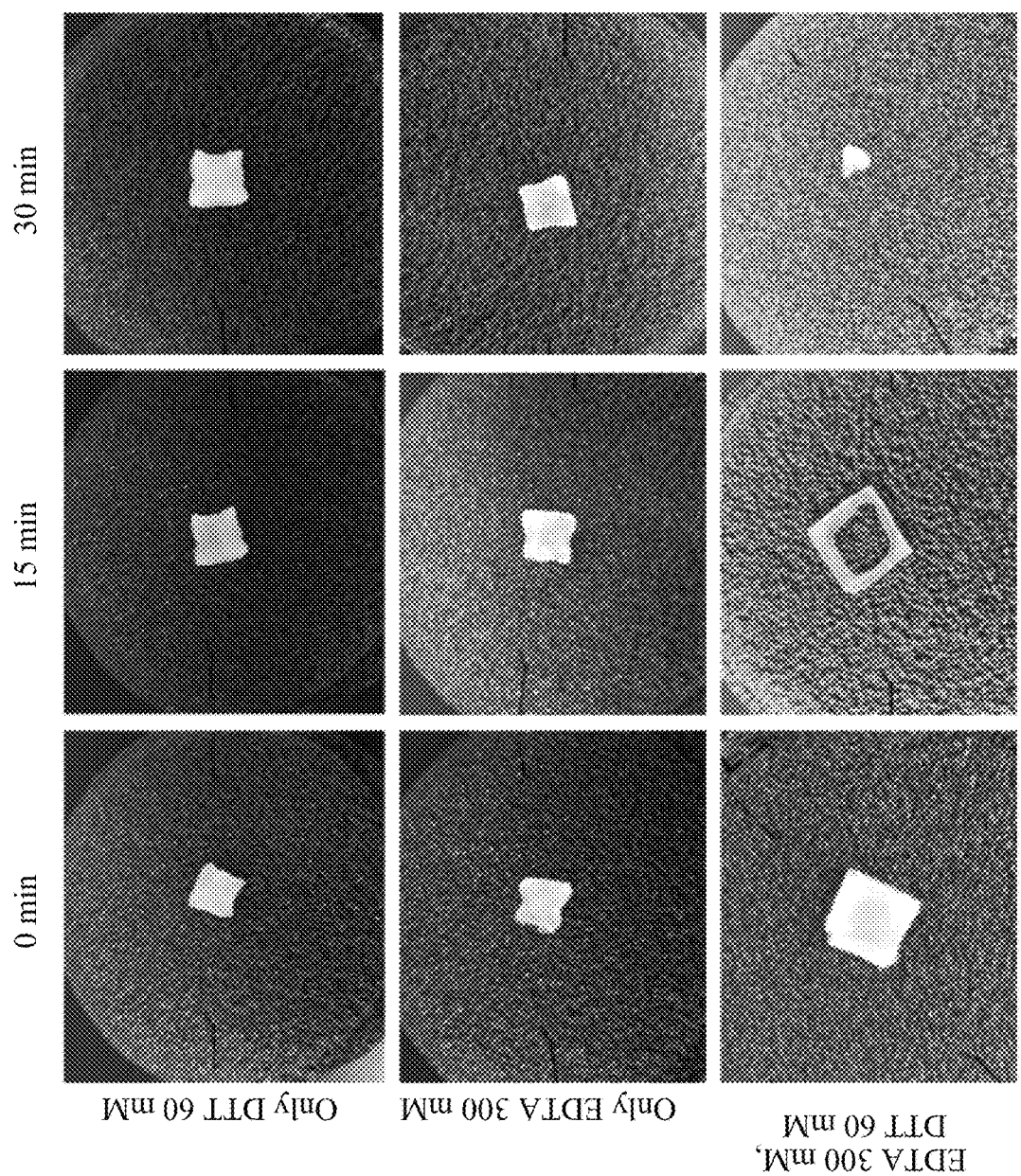
FIG. 8C is a series of photographs showing the hydrogel in different concentrations of crosslinking agents.
Figure 8D:
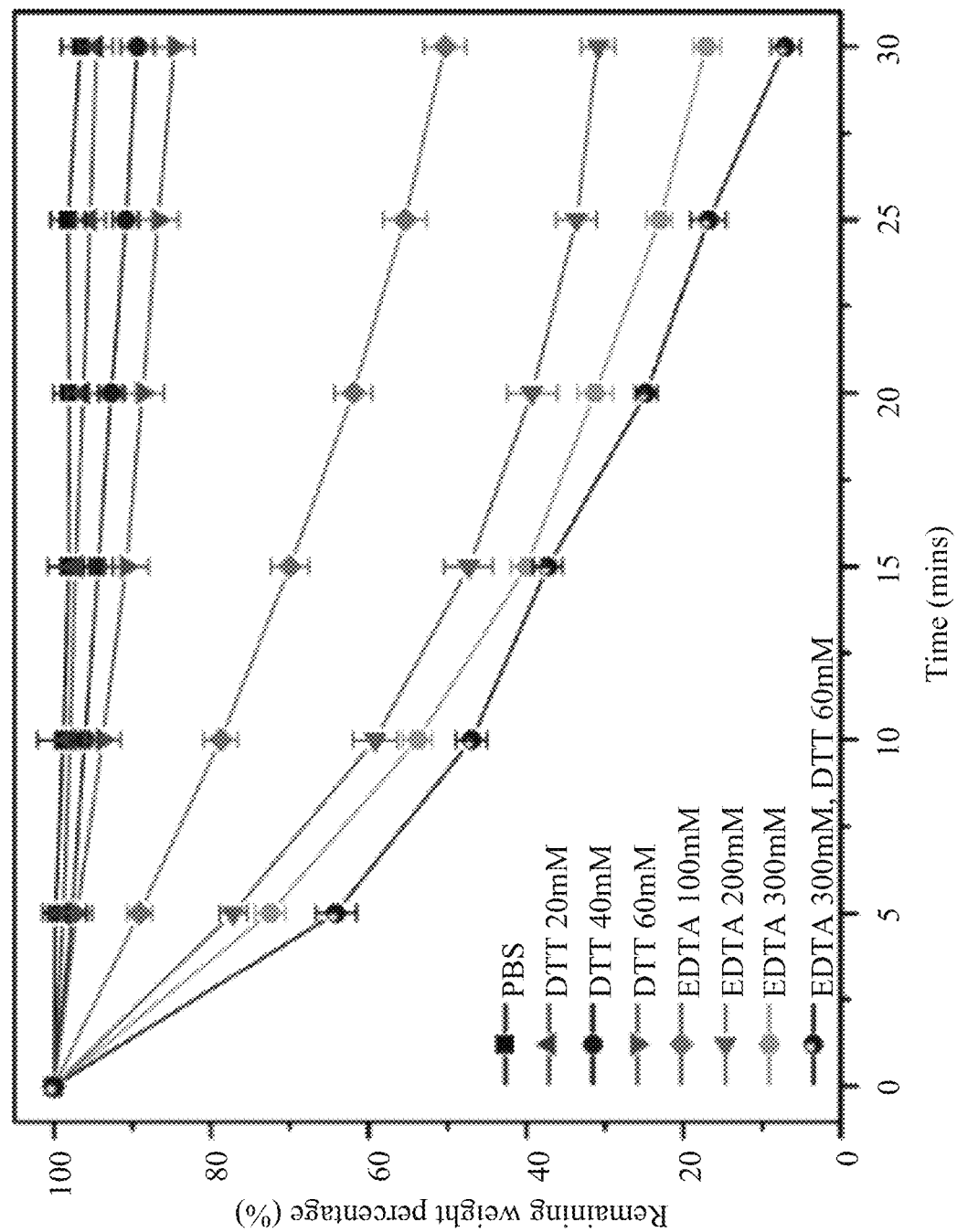
FIG. 8D is a line graph showing disintegration of separable of IPN hydrogel under different disintegrating solutions (n=3).

The effect of the concentration of crosslinker on the rate of degradation of the separable IPN hydrogel are shown in FIGS. 8A and 8B. The hydrogel with a crosslinker concentration of one-hundredth was immersed in a mixture of DTT and EDTA solution (DTT 20 mM, EDTA 100 mM) and was completely disintegrated after 1 hour, while with the crosslinker concentration at one-tenth of the monomer, about 41% of the hydrogel remained within the same period of time (1 hour). The internal structure of the hydrogel with a high concentration of crosslinking agent was relatively dense and hence not easy to disintegrate in a short amount of time. However, at low concentration of crosslinking agent, the presence of void in the internal structure and the increased surface area lead to higher rate of disintegration of IPN hydrogel.

The rate of degradation of the separable hydrogel prepared at cross linker to monomer ratio of 1:100 was also investigated at different aqueous environments including PBS, DTT 20 mM, DTT 40 mM, DTT 60 mM, EDTA 100 mM, EDTA 200 mM, EDTA 300 mM and EDTA 300 mM+DTT 60 mM aqueous solutions. As shown in FIGS. 8C and 8D, minimal disintegration of the hydrogel in PBS solution while only less than 10% of the hydrogel remained in a combined solution of EDTA 300 mM and DTT 60 mM during 30 min incubation. Hence, the rate of disintegration of the disulfide linked IPN hydrogel and separability of MNs can be improved through adjusting the concentration of disintegrating agents.

Skin Penetration Test

Figure 9C:
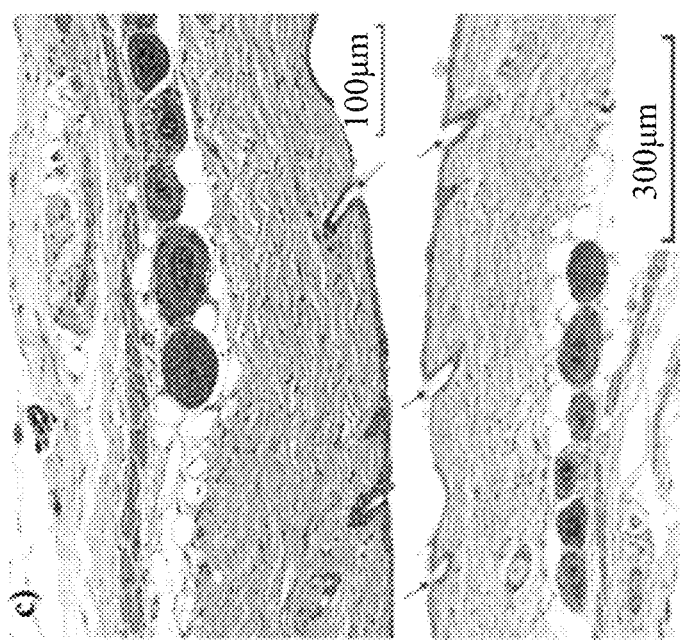
FIG. 9C is a H&E stained image of skin tissue after MNs penetration.
Figure 9E:
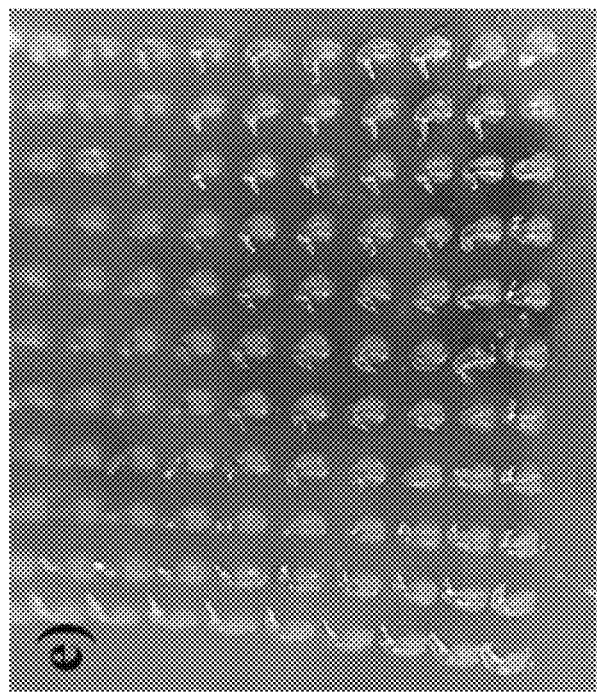
FIG. 9E is a morphology of MNs after skin penetration.

The skin of C57BL/6 mouse was used to test whether the microneedle penetrates into the skin. After the MNs were squeezed into the skin with a fixed force applying device and stained with trypan blue, round holes were observed on the skin under optical microscope (FIG. 9B). The histology of the skin tissue after the penetration of MNs was further examined with H&E staining to investigate the depth of penetration of MNs into the skin. As shown in FIG. 9C, the outer layer of the skin, possibly stratum corneum, was completely penetrated (red arrows) by the MNs. This result suggests that the IPN hydrogel-based MN arrays had enough mechanical strength to penetrate the outer layer of the skin of mice for effective transdermal drug delivery application. As seen in FIG. 9E, the shape of MNs arrays were not markedly deformed after penetration further demonstrated the high mechanical strength of MNs.

In Vitro Drug Loading and Release

Drug release behavior of IPN hydrogel was examined. First, DOX and/or LPS were loaded into the hydrogel by simple mixing with IPN hydrogel pre-gel solution (0.5 mg DOX/MNs and 0.2 mg LPS/MNs) followed by casting MNs and sequential photo-ionic crosslinking to obtained drug loaded solid MNs arrays (DOX loaded MN, LPS loaded MN and LPS/DOX loaded MN). Then, drug loaded MNs were immersed in 10 mL PBS solution and kept in an orbital shaker incubator with a rotation of 100 rpm at 37° C. As shown in FIGS. 10A and 10B, a rapid release of DOX and LPS in the first 4 hours were observed due to high rates of drugs diffusion on the surface of MNs array and then a steady release due to the degradation of MNs. Degradation of IPN hydrogel-based MNs in PBS medium was mainly attributed to sodium-calcium exchange in the hydrogel that enhanced swelling and disintegration of hydrogel for ease drug diffusion. The sodium ions in the PBS slowly exchanged with the calcium ion in alginate segments of the IPN hydrogel and caused disintegration of crosslinker and finally the hydrogel structure was completely collapsed as shown in FIG. 7, and released contents such as remaining drugs, DOX and LPS in the MNs. However, the rapid rate of degradation of the MNs in PBS as shown in FIG. 7 accompanied with the release of nearly 66.1±7.4% and 59.4±5.5% of DOX and LPS, respectively during 24 hours and the remaining drugs were released within about 7 days. This timely release of drugs is one of the advantages for delivering adequate dose of drugs to the target site and achieved an efficient treatment. The relatively slow release rate of LPS than DOX partly due to its larger molecular weight and the chemical structure of repeated carboxylic and phosphate group in LPS that possibly form physical cross linkage in the presence of calcium ion and cause sluggish of release.

Biocompatibility of IPN Hydrogel

Figure 16A:
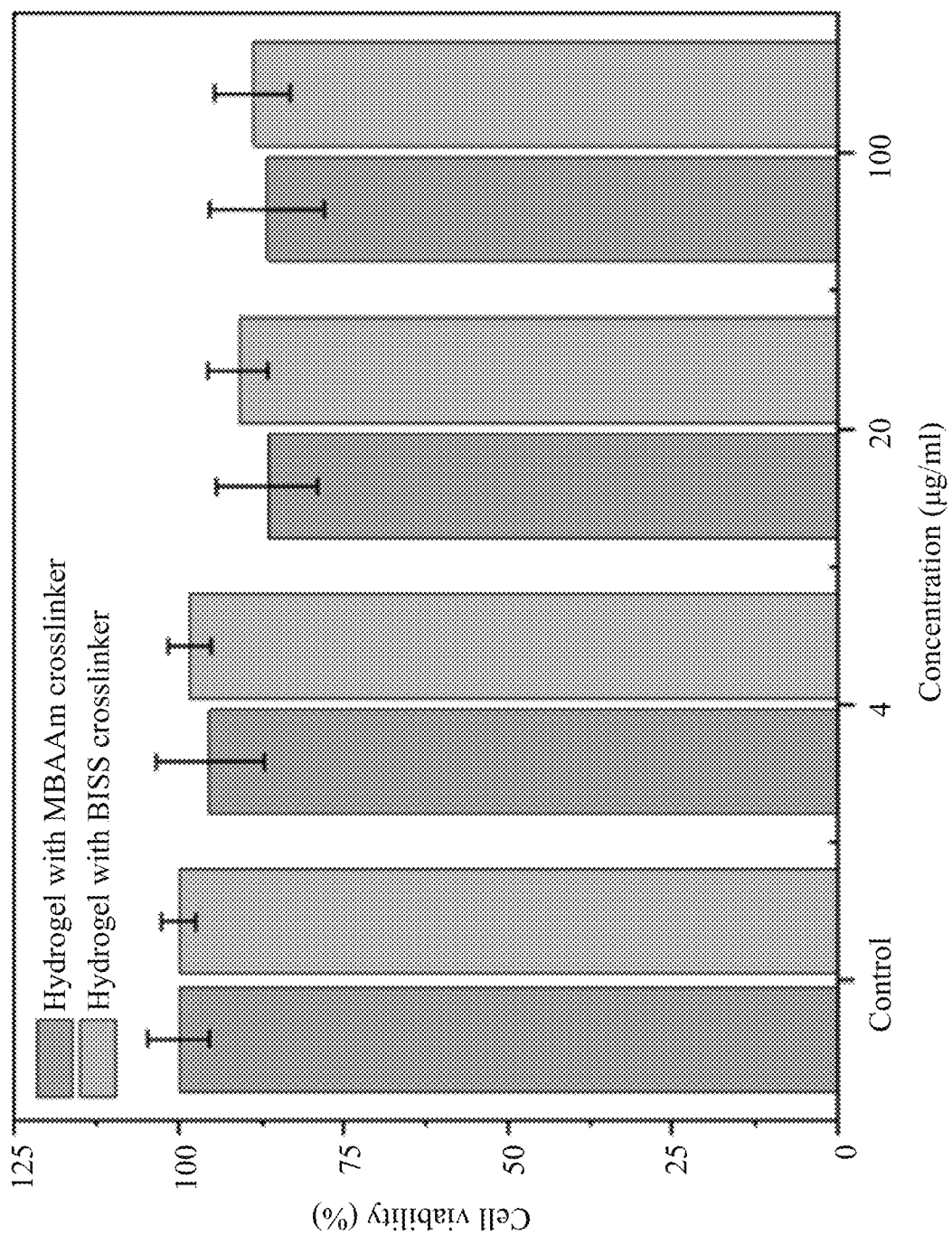
FIGS. 16A and 16B show the result of biocompatibility test (MTT assay) of IPN hydrogel against mouse glioma cells (CT-2A-Luc cells) and mouse embryonic fibroblasts (NIH-3T3 cells), respectively. (n=8)
Figure 16B:
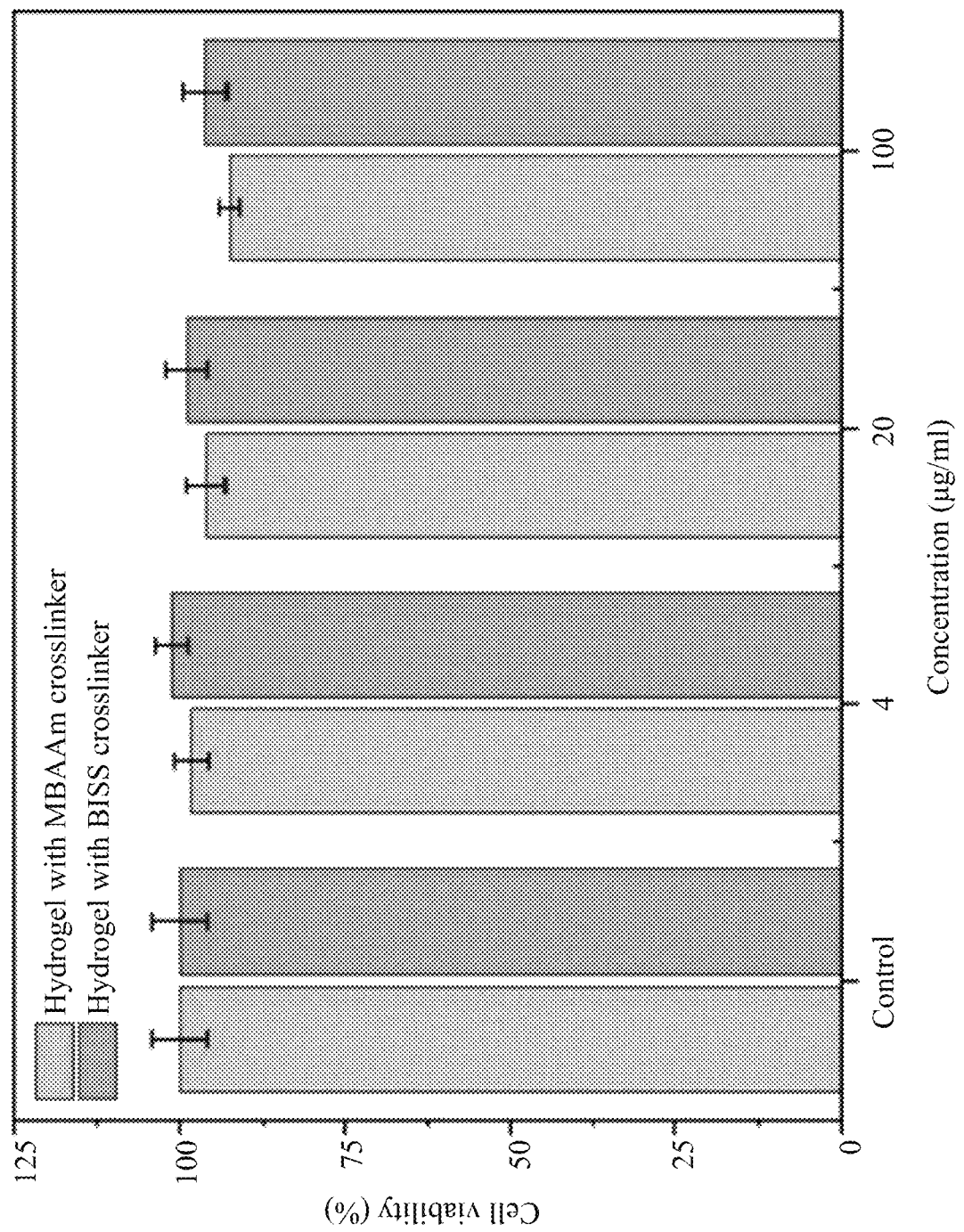

Biocompatibility of the hydrogel is an indispensable concern for in vivo application. Therefore, biocompatibility of the hydrogel was evaluated in vitro through MTT assay against CT-2A-Luc cells and NIH-3T3 cells. After the cells were treated with hydrogel by co-culturing with hydrogel extracts, MTT dye was added and biocompatibility of the hydrogel was determined based on the absorbance intensity of purple crystals at 570 nm in the mitochondria of viable cells. Accordingly, the viability of cells treated with either BISS or MBAAm crosslinked hydrogel was greater than 85% on CT-2A-Luc cells and 92.6% on NIH-3T3 cells, even at high concentration (0.1 g/mL) of the hydrogel sample, suggested that the hydrogels has remarkable biocompatibility and will not affect cells upon delivery into the skin via transdermal drug delivery, as shown in FIG. 16.

Cytotoxicity of DOX Loaded MNs

The anti-cancer effect of DOX loaded MNs was assessed on CT-2A-Luc cells and NIH-3T3 cells by MTT assay. As demonstrated in FIG. 11A, cell viability (%) was significantly decreased with increasing the concentration of DOX which resulted 35.7±4.7% and 41.1±3.4% cell viability on CT-2A-Luc and NIH-3T3 cells, respectively at a maximum concentration of DOX (10 μg/mL), suggested the effectiveness of DOX loaded MNs to treat cancer cells at a considerable concentration. Moreover, the half inhibitory concentration ($IC_{50}$) of DOX loaded MNs estimated using Gaussian equation was 1.088 μg/mL for CT-2A-Luc cells and 3.23 μg/mL for NIH-3T3 cells (FIG. 11B). The lower the value of $IC_{50}$, the stronger the cell growth inhibition ability of the drug. Here in, unlike cancer cells (CT-2A-Luc cells), NIH-3T3 cells were moderately resistant to DOX with a higher $IC_{50}$ value or exhibited better cell viability at the same concentration of DOX which suggests an enhanced DOX internalization in cancerous cells than normal cells.

In Vivo Antitumor Efficacy of Dual Drug Loaded MNS

The efficiency of MNs mediated transdermal co-delivery of LPS and DOX and their synergistic effect on tumor growth inhibition was evaluated on glioma bearing C57BL/6 mice. Obviously, a direct intratumoral (IT), peritumoral (PT) or intravenous (IV) injection of therapeutic agents for tumor suppression may lead to drug leakage to the nearby tissues, thereby decreasing the therapeutic efficacy and safety. However, MNs-mediated localized transdermal drug delivery can circumvent these issues by improving drug diffusion deep to the tumor and result in high tumor accumulation. Moreover, MNs have played important role in combination therapy at which multiple drugs can be loaded in the MNs and applied for synergistic value in sustained manner. Since a high density of immune cells including the langerhans cells (LCs), dendritic cells (DCs) and macrophages are accumulated in the skin tissue, MNs mediated transdermal co-delivery of LPS and DOX would have an efficient synergy of immuno-chemotherapy for cancer treatment. Because, an immunostimulatory molecule, LPS, had a great opportunity to interact and activate those immune cells for enhancing the therapeutic effect of chemo-drug, DOX.

Drug loaded separable MNs (LPS loaded MNs, DOX loaded MNs and LPS/DOX loaded MNs) and blank separable MNs were applied on subcutaneous tumors for transdermal delivery of anti-cancer drugs as described above. The separable substrate of the MNs were removed after 24 h with few droplets of EDTA (300 mM) and DTT (60 mM) which was less than the minimum toxic dosage and then the progress of tumor growth with time was monitored for 18 days by measuring the external tumor volume as shown in FIG. 12B. The drug loaded MNs arrays punctured the stratum corneum of the skin and steadily released drugs locally for efficient tumor suppression. Eventually, the tumor growth profile of each group was summarized in FIGS. 12A and 12B.

The mice treated with drug loaded MNs showed significant inhibition on tumor growth as compared with the control group (non-treated) or the mice treated with blank MNs that manifested a rapid tumor growth. At the end of the treatment period (18 days), the average tumor volume of mice treated with LPS loaded MNs, DOX loaded MNs and LPS/DOX loaded MNs was 552.4±205.6 mm$^3$, 345.4±220.2 mm$^3$ and 253.0±176.9 mm$^3$, respectively, which was significantly lower than the control group (1696.8±447.6 mm$^3$) or mice treated with blank MNs (1468.31±460.68 mm$^3$), as shown in FIG. 12A. Remarkably, the tumor growth on mice treated with dual drugs (LPS/DOX loaded MNs) was greatly inhibited than even the DOX loaded MNs treated one. This might be attributed to the synergistic effect of chemo-drug (DOX) and the prominent immunostimulatory effect of LPS that accompanied with upregulation of different anti-cancer immune cells. The photographs of tumor in FIG. 12B also showed parallel trends that the size of tumors treated with LPS/DOX loaded MNs was significantly smaller than other formulations. Moreover, the weight of tumor shown in FIG. 12C, further verified that the dual drugs (LPS/DOX loaded MNs) has better tumor growth inhibition than the individual drugs (LPS loaded MNs or DOX loaded MNs). The average body weight of different treatment groups (21.8±1.1 to 23.3±0.5 g) was not significantly altered and no death of animals during the treatment period. However, unlike the control group, the body weight of the mice treated with MNs was distinctly dropped in the first 2 days of treatment and then increased in parallel as the control group, as shown in FIG. 12D. This is due to anesthesia injection at the time of fixing the separable MNs on the tumor and the MNs discomfort to the mice until the separable substrate was removed in 24 hours. As provided herein, the separable MNs is convenient and efficient for transdermal delivery of anti-cancer drugs at proximity and provides a method to minimize this the systemic toxicity and side effects of the drugs.

Immunohistochemistry

LPS is able to inhibit the apoptosis of dendritic cells (DC) and enhance DC-mediated proliferation of CD4+ T cells, up-regulation of CD80, CD86, CD69 and CD25 expressions and cytokine secretion such as TNF-α and IL-6. Therefore, to elucidate the immunostimulatory effect of LPS for anticancer activity in vivo, the spleen and tumor tissues of each group were harvested and stained for examining CD25+, CD4+, CD69+, CD8+, TNF-α and activated caspase 3 levels as a representative immunoregulator biomarkers. The histopathological data was generated by examination of H&E-stained slides using light microscope and the percentage of the affected organ for both proliferative and non-proliferative changes in laboratory animals was based on the International Harmonization of Nomenclature and Diagnostic Criteria (INHAND).

CD25+ is a type I transmembrane protein present on activated T cells and activated B cells and appears to be a reliable immunohistochemical marker for the upregulation of immune cells. As a result, CD25+ was highly expressed mainly on mice treated with LPS containing MNs and positive signals were mostly presented in the splenic sinus of red pulp, but scant signals also present in the germinal center of the spleen. The quantity of positive signals was predominantly higher in LPS/DOX loaded MNs treated group than other groups. It was also manifested that the CD4+ and CD69+ T cells were markedly upregulated on spleen tissue of mice treated with LPS (LPS loaded MNs and LPS/DOX loaded MNs) while relatively lower in the control group, indicated the activation and proliferation of the major antigen presenting cells, B cells, by LPS, as shown in FIG. 13A. The positive signals were frequently present in the periarteriolar lymphoid sheath (PALS) in germinal center or in the splenic sinus of red pulp. The expression of CD8+ T cells and TNF-α on tumor tissue were largely increased on LPS treated tumor tissues accompanied with tumor growth suppression, suggested that LPS enabled local potentiation of immune cells for cancer immunotherapy. LPS stimulates monocytes to be transformed into M1 macrophages which subsequently played an important role in vanishing cancer cells through direct attack or indirectly by recruiting other immune cells or secreting various cytokines. Positive signals of CD8+ was frequently presented in the necrotic tissue and peri-tumor area, while TNF-α was mainly presented in neoplastic cells and inflammatory cells in peri-tumor tissues. Although there were no neoplastic cells in LPS/DOX loaded MNs, significantly higher TNF-α signals were noted in some inflammatory cells in connected tissues, suggested that the combined drugs effectively eliminate cancer cells.

Cleaved caspase 3 or activated caspase 3 is another biomarker of apoptotic cells which enable degradation of multiple cellular proteins and DNA fragmentation in cells during apoptosis and the findings was obtained from the IHC examination as shown in FIG. 13B, indicated an over expression of cleaved caspase 3 on tumor tissues of groups 3, 4 & 5 which verified that cancer cells underwent apoptosis mainly in response to combined drugs (LPS/DOX/MNs) and progression of tumor was notably inhibited. The results were consistent with reduced tumor size demonstrated in FIG. 12 above.

The positive signals were frequently present in central necrotic and peri-necrotic area and it was strong in cytoplasm and nucleus of the cells. Recently, despite a great clinical success has been achieved from chemotherapy, its effectiveness is strongly influenced by heterogeneous tumor microenvironment. On the other hand, immunotherapy or cancer vaccination that relies on regulation of the patient's immune system to recognize and destruct malignant cells has paradigm shift in cancer treatment. However, most biomolecules such as peptides and nucleic acids which are injected to the circulatory system as a vaccine are more susceptible to enzymatic degradation in the body fluid. The maneuvered use of MNs as a vehicle for transdermal delivery of immunostimulatory molecules or vaccines is, therefore, a major breakthrough of cancer immunotherapy at which biomolecules are shielded from enzymatic attack and delivered into the skin where APCs are highly populated.

Hereof, MN arrays traverse the stratum corneum and convey LPS to the immune-cell-rich epidermis and elicit a wide range of immune responses including maturation of DCs. Subsequently, maturation of DCs enabled to activate B cells and CD8+ T cells for humoral and cellular immunity, respectively and provided synergistic value for chemotherapy. Hence, MNs-mediated transdermal delivery system is an appealing approach in cancer immunogenicity and treatment.

What is claimed is:

1. A transdermal delivery device, comprising:
a plurality of projections each including a first polymer formed of a first monomer with a first linkage and a second polymer formed of a second monomer with a second linkage;
a substrate including a third polymer formed of the first monomer with a third linkage; and
a bioactive agent comprised in one of the plurality of projections,
wherein the plurality of projections are coupled to the substrate and configured to be at least partially insertable into skin of a subject in need thereof, and the substrate is configured to be removed with a compound targeted to break the third linkage forming the third polymer in the substrate after the transdermal delivery device is applied to the skin for a predetermined time, and
wherein the compound targeted to break the third linkage forming the third polymer in the substrate is dithiothreitol (DTT), ethylenediaminetetraacetic acid (EDTA), glutathione (GSH), β-mercaptoethanol or L-cysteine.

2. The transdermal delivery device according to claim 1, wherein the first monomer is a zwitterion.

3. The transdermal delivery device according to claim 2, wherein the zwitterion is phosphorylcholine, sulfobetaine, pyridinium alkyl sulfonate, carboxybetaine, phosphobetaine, phosphonobetaine, phosphinobetaine, ammoniosulfate, ammoniosulfonamide, pyridiniocarboxylate or sulfoniocarboxylate.

4. The transdermal delivery device according to claim 3, wherein the phosphorylcholine is phosphorylcholine acrylate, phosphorylcholine acrylamide, phosphorylcholine methacrylate, alkoxydicyanoethenolate or 2-methacryloyloxyethyl phosphorylcholine.

5. The transdermal delivery device according to claim 3, wherein the sulfobetaine is sulfobetaine acrylate, sulfobetaine acrylamide, sulfobetaine methacrylate, sulfobetaine vinylimidazole or sulfobetaine vinylpyridine.

6. The transdermal delivery device according to claim 3, wherein the carboxybetaine is carboxybetaine acrylate, carboxybetaine methacrylate, carboxybetaine acrylamide, carboxybetaine vinylimidazole, carboxybetaine methacrylamide, carboxybetaine isobutylene or carboxybetaine diallylamine.

7. The transdermal delivery device according to claim 3, wherein the pyridinium alkyl sulfonate is 3-(2-vinylpyridinium-1-yl) propane-1-sulfonate, N-(2-methacryloyloxy) ethyl-N,N-dimethylammoniopropanesulfonate or N-(3-methacryloylimino) propyl-N,N- dimethylammoniopropanesulfonate.

8. The transdermal delivery device according to claim 1, wherein the second polymer is one or more selected from the group consisting of a biocompatible synthetic polymer, a semisynthetic polymer and a natural polymer.

9. The transdermal delivery device according to claim 1, wherein the second polymer is selected from the group consisting of gum, polysaccharide, a polysaccharide derivative, alginate including sodium alginate or calcium alginate, chitosan, a chitosan derivative, collagen, gelatin, dextran, poly (vinylpyrrolidone), hydroxyethyl (heta) starch, polyethylene glycol, functionalized dextran, glycopolymer containing trehalose, hyaluronic acid, methacrylated hyaluronic acid, poly (methyl vinyl ether), poly (methyl vinyl ether-alt-maleic anhydride), poly (lactic acid), polyglycolide, poly (lactic-co- glycolic acid), polycarbonate, poly (vinyl alcohol), poly (hydroxyethyl methacrylate), poly (vinylpyrrolidone), (2-carboxymethyl)-3-acrylamidopropyl dimethylammonium bromide, (2-carboxymethyl)-3-acrylamidopropyl dimethylammonium bromide-co- hydroxyethyl methacrylate, (2-carboxymethyl)-3-acrylamidopropyl dimethylammonium bromide-co-acrylamide, methacrylated (2-carboxymethyl)-3-acrylamidopropyl dimethylammonium bromide-co-acrylamide, poly (ε-caprolactone) poly (ε-aprolactone- co-glycolic acid), poly (2-methacryloyloxyethyl phosphorylcholine), poly (carboxybetaine) vinylimidazole, poly (sulfobetaine) vinylimidazole, and poly (sulfobetaine) vinylpyridine.

10. The transdermal delivery device according to claim 1, wherein the first monomer is crosslinked by a chemical linkage and the second monomer is crosslinked by a physical linkage.

11. The transdermal delivery device according to claim 10, wherein the chemical linkage and the physical linkage forms an interpenetrating polymer network.

12. The transdermal delivery device according to claim 10, wherein the chemical linkage is formed by at least one crosslinking agent selected from the group consisting of N,N'-methylene-bisacrylamide (MBA), diacryloyl derivative of cystine (BISS), dimethylsubermidate, glutaraldehyde, N,N-ethylene-bis (iodoacetamide), ethylene glycol dimethacrylate (EGDM), poly (ε-caprolactone) diacrylate, polylactide diacrylate, polylactide dimethacrylate, poly (lactide-co-glycolide) diacrylate, poly (lactide-co-glycolide) dimethacrylate, poly (ε-caprolactone-b-ethylene glycol-b-ε-caprolactone) diacrylate, glycol-b-(lactide-co-glycolide) dimethacrylate, a polymerizable compound including a disulfide bond, a peptide bond or an ester bond, poly (ε-caprolactone) dimethacrylate (MAC-PCL-MAC), poly (ε-caprolactone-b-ethylene glycol-b-ε-caprolactone) dimethacrylate (MAC-PCL-PEG-PCL-MAC), poly (lactide-b-ethylene glycol-b-lactide) diacrylate (AC-PLA-PEG-PLA-AC), poly (lactide-b-ethylene glycol-b-lactide) dimethacrylate (MAC-PLA-PEG-PLA-MAC), poly [(lactide-co-glycolide)-b-ethylene glycol-b-(lactide-co-glycolide)] diacrylate (AC-PLGA-PEG-PLGA-AC), poly [(lactide-co-glycolide)-b-ethylene glycol-b-(lactide-co-glycolide)] dimethacrylate (MAC-PLGA-PEG-PLGA-MAC), poly (ε-caprolactone-co-lactide)-diacrylate (AC-PCLA-AC), poly (ε-caprolactone-co-lactide) dimethacrylate (MAC-PCLA-MAC), poly (ε-caprolactone-co-glycolide) diacrylate (AC-PCGA-AC), poly (ε-caprolactone-co-glycolide) dimethacrylate (MAC-PCGA-MAC), poly (ε-caprolactone-co-lactide) -b-ethyleneglycol-b-(ε-caprolactone-co-lactide) diacrylate (AC-PCLA-PEG-PCLA-AC), poly (ε-caprolactone-co-lactide)-b-ethyleneglycol-b-(ε-caprolactone-co-lactide) dimethacrylate (MAC-PCLA-PEG-PCLA-MAC), poly (ε-caprolactone-co-glycolide)-b-ethyleneglycol-b-(ε-caprolactone-co-glycolide) diacrylate (AC-PCGA-PEG-PCGA-AC), and poly (ε-caprolactone-co-glycolide)-b-ethyleneglycol-b-(ε-caprolactone-co-glycolide) dimethacrylate (MAC-PCGA-PEG-PCGA-MAC).

13. The transdermal delivery device according to claim 10, wherein a ratio between the first monomer and the second monomer is about 1:1, about 1:2, about 1:3, about 1:4, about 1:5, about 2:1, about 3:1, about 4:1 or about 5:1.

14. The transdermal delivery device according to claim 1, wherein the third linkage is a disulfide bond.

15. The transdermal delivery device according to claim 1, wherein the plurality of projections each have a shape tapered to a point.

16. The transdermal delivery device according to claim 15, wherein the plurality of projections each have a pyramidal shape or a conical shape.

17. The transdermal delivery device according to claim 15, wherein the plurality of projections each have a height of between about 25 μm to about 2,500 μm, a width of between about 50 μm to about 250 μm, and a diameter of tip between about 1 μm to about 25 μm.

18. A method of fabricating a transdermal delivery device according to claim 1, the method comprising:
  preparing a first solution including the first monomer, the second monomer, a first crosslinking agent, and at least one bioactive agent;
  preparing a second solution including the first monomer and a second crosslinking agent;
  applying the first solution including the at least one bioactive agent to an inverse mold and subjecting the first solution to centrifuge;
  after centrifugation, removing an upper layer of the first solution and applying the second solution on a top of the inverse mold;
  covering the inverse mold with a cover mold and subjecting to centrifuge;
  applying a first condition suitable to cause solidification of the first solution to form the plurality of projections;
  applying a second condition suitable to cause solidification of the second condition to form the substrate; and
  demolding the plurality of projections and the substrate from the inverse mold to obtain the transdermal delivery device.

19. A method of inducing a biological activity in a subject in need thereof, comprising:
  providing the transdermal delivery device of claim 1;
  applying the transdermal delivery device to the skin of the subject for the plurality of projections to puncture the skin of the subject; and
  removing the substrate of the transdermal delivery device from the subject with a compound targeted to break the third linkage forming the third polymer in the substrate, with the plurality of projections including the bioactive agent to be remained in the skin.

* * * * *